United States Patent
Colton et al.

(10) Patent No.: US 9,447,378 B2
(45) Date of Patent: Sep. 20, 2016

(54) METHOD FOR DIFFERENTIATING HUMAN EMBRYONIC STEM CELLS INTO β-CELLS FOR THE TREATMENT OF TYPE I DIABETES

(71) Applicant: Massachusetts Institute of Technology, Cambridge, MA (US)

(72) Inventors: Clark K. Colton, Newton, MA (US); Amanda Dilenno, Boston, MA (US); Jeffrey R. Millman, St. Louis, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 13/873,020

(22) Filed: Apr. 29, 2013

(65) Prior Publication Data
US 2013/0287743 A1    Oct. 31, 2013

Related U.S. Application Data

(60) Provisional application No. 61/639,794, filed on Apr. 27, 2012.

(51) Int. Cl.
| | | |
|---|---|---|
| *C12N 5/00* | (2006.01) | |
| *C12N 5/02* | (2006.01) | |
| *C12N 5/071* | (2010.01) | |
| *C12N 5/0735* | (2010.01) | |

(52) U.S. Cl.
CPC ........... *C12N 5/0606* (2013.01); *C12N 5/0676* (2013.01); *C12N 2500/02* (2013.01); *C12N 2506/02* (2013.01)

(58) Field of Classification Search
CPC .................... C12N 2506/02; C12N 5/0606
See application file for complete search history.

(56) References Cited

U.S. PATENT DOCUMENTS

| | | |
|---|---|---|
| 5,134,057 A | 7/1992 | Kuypers et al. |
| 5,314,960 A | 5/1994 | Spinelli et al. |
| 5,942,435 A | 8/1999 | Wheeler |
| 6,534,052 B1 | 3/2003 | Xiao et al. |
| 6,613,568 B2 | 9/2003 | Kaufman et al. |
| 6,833,269 B2 | 12/2004 | Carpenter |
| 7,033,831 B2 | 4/2006 | Fisk et al. |
| 7,250,294 B2 | 7/2007 | Carpenter et al. |
| 7,282,366 B2 | 10/2007 | Rambhatla et al. |
| 7,326,572 B2 | 2/2008 | Fisk et al. |
| 7,425,448 B2 | 9/2008 | Xu |
| 7,732,199 B2 | 6/2010 | Xu |
| 7,763,464 B2 | 7/2010 | Xu |
| 9,029,147 B2 | 5/2015 | Colton et al. |
| 2002/0120084 A1 | 8/2002 | Valint et al. |
| 2005/0164382 A1 | 7/2005 | Xu |
| 2005/0266554 A1 | 12/2005 | D'Amour et al. |
| 2007/0259421 A1 | 11/2007 | D'Amour et al. |
| 2010/0261277 A1 | 10/2010 | Colton et al. |
| 2011/0312087 A1 | 12/2011 | Khan |
| 2012/0219532 A1 | 8/2012 | Colton et al. |
| 2014/0370598 A1 | 12/2014 | Colton et al. |

FOREIGN PATENT DOCUMENTS

| | | |
|---|---|---|
| WO | WO 00/29550 A2 | 5/2000 |
| WO | WO 2008/156708 A2 | 12/2008 |
| WO | WO 2009/007852 A2 | 1/2009 |
| WO | WO 2009/035217 A1 | 3/2009 |
| WO | WO 2009/079007 A1 | 6/2009 |
| WO | WO 2011/005326 A1 | 1/2011 |

OTHER PUBLICATIONS

Mfopou, 2014, Stem Cell Research, 12:166-177.*
Van Hoof, 2011, Stem Cell Research, 6:276-285.*
D'Amour et al., Production of pancreatic hormone-expressing endocrine cells from human embryonic stem cells. Nature Biotech. Nov. 2006;24(11):1392-401.
Kroon et al., Pancreatic endoderm derived from human embryonic stem cells generates glucose-responsive insulin-secreting cells in vivo. Nat Biotechnol. Apr. 2008;26(4):443-52.
Zandstra et al., Scalable production of embryonic stem cell-derived cardiomyocytes. Tissue Eng. Aug. 2003;9(4):767-78.
[No Author Listed], FDA Center for Biologics Evaluation and Research: Cellular, Tissue, and Gene Therapeutics Advisory Committee, Summary Minutes. Meeting #45. Apr. 10-11, 2008. 7 pages.
[No Author Listed], Innovative cell culture devices to help expand your growth. Wilson Wolf Manufacturing, Inc. http://www.wilsonwolf.com/technology.htm [last accessed Jun. 4, 2008]. 1 page.
Ai et al., Biocompatibility of layer-by-layer self-assembled nanofilm on silicone rubber for neurons. J Neurosci Methods. Sep. 30, 2003;128(1-2):1-8.
Avgoustiniatos, Oxygen diffusion limitations in pancreatic islet culture and immunoisolation. Thesis; Massachusetts Institute of Technology. Feb. 2002. 648 pages.
Baharvand et al., Differentiation of human embryonic stem cells into hepatocytes in 2D and 3D culture systems in vitro. Int J Dev Biol. 2006;50(7):645-52.
Bauwens et al., Development of a perfusion fed bioreactor for embryonic stem cell-derived cardiomyocyte generation: oxygen-mediated enhancement of cardiomyocyte output. Biotechnol Bioeng. May 20, 2005;90(4):452-61.
Bjorklund et al., Embryonic stem cells develop into functional dopaminergic neurons after transplantation in a Parkinson rat model. Proc Natl Acad Sci U S A. Feb. 19, 2002;99(4):2344-9. Epub Jan. 8, 2002.
Blum et al., Clonal analysis of human embryonic stem cell differentiation into teratomas. Stem Cells. Aug. 2007;25(8):1924-30. Epub Apr. 26, 2007.

(Continued)

*Primary Examiner* — Valarie Bertoglio
(74) *Attorney, Agent, or Firm* — Wolf, Greenfield & Sacks, P.C.

(57) ABSTRACT

The invention provides inter alia methods for differentiating embryonic stem cells into insulin producing cells, as well as compositions comprising such cells, and therapeutic uses of such compositions.

16 Claims, 21 Drawing Sheets

(56) References Cited

OTHER PUBLICATIONS

Blum et al., The tumorigenicity of human embryonic stem cells. Adv Cancer Res. 2008;100:133-58.

Bondue et al., Mesp1 acts as a master regulator of multipotent cardiovascular progenitor specification. Cell Stem Cell. Jul. 3, 2008;3(1):69-84.

Bonner-Weir et al., In vitro cultivation of human islets from expanded ductal tissue. Proc Natl Acad Sci U S A. Jul. 5, 2000;97(14):7999-8004.

Brederlau et al., Transplantation of human embryonic stem cell-derived cells to a rat model of Parkinson's disease: effect of in vitro differentiation on graft survival and teratoma formation. Stem Cells. Jun. 2006;24(6):1433-40. Epub Mar. 23, 2006.

Brunelle et al., Oxygen deprivation induced cell death: an update. Apoptosis. Dec. 2002;7(6):475-82.

Brusselmans et al., A novel role for vascular endothelial growth factor as an autocrine survival factor for embryonic stem cells during hypoxia. J Biol Chem. Feb. 4, 2005;280(5):3493-9. Epub Nov. 29, 2004.

Caspi et al., Transplantation of human embryonic stem cell-derived cardiomyocytes improves myocardial performance in infarcted rat hearts. J Am Coll Cardiol. Nov. 6, 2007;50(19):1884-93. Epub Oct. 23, 2007.

Csete, Oxygen in the cultivation of stem cells. Ann N Y Acad Sci. May 2005;1049:1-8.

Cunningham et al., Quantification of fibronectin adsorption to silicone-rubber cell culture substrates. Biotechniques. Apr. 2002;32(4):876-87.

D'Amour et al., Efficient differentiation of human embryonic stem cells to definitive endoderm. Nat Biotechnol. Dec. 2005;23(12):1534-41. Epub Oct. 28, 2005.

Daley et al., Realistic prospects for stem cell therapeutics. Hematol. Am Soc Hematol Educ Program. 2003:398-418.

Damjanov et al., The terminology of teratocarcinomas and teratomas. Nat Biotechnol. Nov. 2007;25(11):1212.

Dang et al., Controlled, scalable embryonic stem cell differentiation culture. Stem Cells. 2004;22(3):275-82.

David et al., MesP1 drives vertebrate cardiovascular differentiation through Dkk-l-mediated blockade of Wnt-signalling. Nat Cell Biol. Mar. 2008;10(3):338-45. Epub Feb. 24, 2008.

Diienno et al., Controlled Oxygen Markedly Influences Differentiation of Embryonic Stem Cells to Insulin Producing Cells. ISSCR 10th Annual Meeting, Yokohama, Japan. Abstract. Jun. 13-16, 2012. 1 page.

Diienno et al., Stable Feeder-and Xeno-free Surfaces for Long-term Growth of Undifferentiated Human Embryonic Stem Cells. Poster. Cambridge, Massachusetts. MIT: Department of Engineering. Jul. 8, 2013. 1 page.

Diienno et al., Variation of Oxygen in a Controlled Manner Markedly Enhances Multi-Stage Differentiation of Embryonic Stem Cells to Insulin Producing Cells. Biomedical Applications of Chemical Engineering 2012 Annual Meeting. Abstract. Oct. 31, 2012. 4 pages.

Drukker et al., Human embryonic stem cells and their differentiated derivatives are less susceptible to immune rejection than adult cells. Stem Cells. Feb. 2006;24(2):221-9. Epub Aug. 18, 2005.

Erdö et al., Host-dependent tumorigenesis of embryonic stem cell transplantation in experimental stroke. J Cereb Blood Flow Metab. Jul. 2003;23(7):780-5.

Fehling et al., Tracking mesoderm induction and its specification to the hemangioblast during embryonic stem cell differentiation. Development. Sep. 2003;130(17):4217-27.

Fernandes et al., Different stages of pluripotency determine distinct patterns of proliferation, metabolism, and lineage commitment of embryonic stem cells under hypoxia. Stem Cell Res. Jul. 2010;5(1):76-89. Epub Apr. 22, 2010.

Fraker et al., Enhanced oxygenation promotes beta-cell differentiation in vitro. Stem Cells. Dec. 2007;25(12):3155-64. Epub Aug. 30, 2007.

Fukuda et al., Stem cells as a source of regenerative cardiomyocytes. Circ Res. Apr. 28, 2006;98(8):1002-13.

Gerecht-Nir et al., Human embryonic stem cells as an in vitro model for human vascular development and the induction of vascular differentiation. Lab Invest. Dec. 2003;83(12):1811-20.

Ginis et al., Differences between human and mouse embryonic stem cells. Dev Biol. May 15, 2004;269(2):360-80.

Grapin-Botton et al., Endoderm development: from patterning to organogenesis. Trends Genet. Mar. 2000;16(3):124-30.

Gu et al., Direct lineage tracing reveals the ontogeny of pancreatic cell fates during mouse embryogenesis. Mech Dev. Jan. 2003;120(1):35-43.

Hentze et al., Cell therapy and the safety of embryonic stem cell-derived grafts. Trends Biotechnol. Jan. 2007;25(1):24-32. Epub Nov. 3, 2006.

Hoffman et al., Characterization and culture of human embryonic stem cells. Nat Biotechnol. Jun. 2005;23(6):699-708.

Horton et al., Engineering microenvironments for embryonic stem cell differentiation to cardiomyocytes. Regen Med. Sep. 2009;4(5):721-32.

Hrvatin et al., Differentiated human stem cells resemble fetal, not adult, β cells. Proc Natl Acad Sci. Feb. 25, 2014;111(8):3038-43. doi: 10.1073/pnas.1400709111.

Humphrey et al., Maintenance of pluripotency in human embryonic stem cells is STAT3 independent. Stem Cells. 2004;22(4):522-30.

Jaenisch et al., Stem cells, the molecular circuitry of pluripotency and nuclear reprogramming. Cell. Feb. 22, 2008;132(4):567-82.

Jensen et al., Diffusion in tissue cultures on gas-permeable and impermeable supports. J Theor Biol. Feb. 1976;56(2):443-58.

Kaufman et al., Hematopoietic colony-forming cells derived from human embryonic stem cells. Proc Natl Acad Sci U S A. Sep. 11, 2001;98(19):10716-21. Epub Sep. 4, 2001.

Kehat et al., Human embryonic stem cells for myocardial regeneration. Heart Fail Rev. Jul. 2003;8(3):229-36.

Keller. Embryonic stem cell differentiation: emergence of a new era in biology and medicine. Genes Dev. May 15, 2005;19(10):1129-55.

Kim et al., Dopamine neurons derived from embryonic stem cells function in an animal model of Parkinson's disease. Nature. Jul. 4, 2002;418(6893):50-6. Epub Jun. 20, 2002.

Kim et al., Increase in dopaminergic neurons from mouse embryonic stem cell-derived neural progenitor/stem cells is mediated by hypoxia inducible factor-1alpha. J Neurosci Res. Aug. 15, 2008;86(11):2353-62.

Klug et al., Genetically selected cardiomyocytes from differentiating embronic stem cells form stable intracardiac grafts. J Clin Invest. Jul. 1, 1996;98(1):216-24.

Koay et al., Hypoxic chondrogenic differentiation of human embryonic stem cells enhances cartilage protein synthesis and biomechanical functionality. Osteoarthritis Cartilage. Dec. 2008;16(12):1450-6. Epub Jun. 9, 2008.

Kurosawa et al., Effect of oxygen on in vitro differentiation of mouse embryonic stem cells. J Biosci Bioeng. Jan. 2006;101(1):26-30.

Laflamme et al., Cardiomyocytes derived from human embryonic stem cells in pro-survival factors enhance function of infarcted rat hearts. Nat Biotechnol. Sep. 2007;25(9):1015-24. Epub Aug. 26, 2007.

Lam et al., Multipotent progenitor cells in regenerative cardiovascular medicine. Pediatr Cardiol. Jul. 2009;30(5):690-8. Epub May 5, 2009.

Lavon et al., Differentiation and isolation of hepatic-like cells from human embryonic stem cells. Differentiation. Jun. 2004;72(5):230-8.

Lawrenz et al., Highly sensitive biosafety model for stem-cell-derived grafts. Cytother. 2004;6(3):212-22.

Lee et al., Efficient generation of midbrain and hindbrain neurons from mouse embryonic stem cells. Nat Biotechnol. Jun. 2000;18(6):675-9.

Lensch et al., the terminology of teratocarcinomas and teratomas. Nat Biotechnol. Nov. 2007;25(11):1211; author reply 1211-2.

Leor et al., Human embryonic stem cell transplantation to repair the infarcted myocardium. Heart. Oct. 2007;93(10):1278-84. Epub Jun. 12, 2007.

(56) References Cited

OTHER PUBLICATIONS

Lindsley et al., Mesp1 coordinately regulates cardiovascular fate restriction and epithelial-mesenchymal transition in differentiating ESCs. Cell Stem Cell. Jul. 3, 2008;3(1):55-68.

Ma et al., Hypoxia and stem cell-based engineering of mesenchymal tissues. Biotechnol Prog. Jan.-Feb. 2009;25(1):32-42. doi: 10.1002/btpr.128. Epub Jan. 1, 2010. 18 pages.

McLimans et al., Kinetics of gas diffusion in mammalian cell culture systems. I. Experimental. Biotechnol Bioeng. Nov. 1968;10:725-40.

Millman et al., Culture under low oxygen conditions markedly enhances differentiation of murine embryonic stem cells into cardiomyocytes, The 5th International Society for Stem Cell Research (ISSCR) Annual Meeting, Cairns, Australia. Jun. 17-20, 2007. 1 page.

Millman et al., Differentiation of murine embryonic stem cells under low oxygen influences cardiomyocyte yield and timing and magnitude of cardiomyocyte gene expression. NIH Symposium on Cardiovascular Regenerative Medicine, Bethesda, MD. Oct. 14-15, 2009. 1 page.

Millman et al., Extended Low Oxygen Culture of Mouse Embryonic Stem Cells Reduces the Fraction of Tumor-Forming Residual Pluripotent Cells in Differentiated Populations. NIH Symposium on Cardiovascular Regenerative Medicine, Bethesda, MD. Oct. 14-15, 2009. 1 page.

Millman et al., Low oxygen influences the self-renewal and differentiation of murine embryonic stem cells, The 6th International Society for Stem Cell Research (ISSCR) Annual Meeting, Philadelphia, PA. Jun. 11-14, 2008. 1 page.

Millman et al., The effects of low oxygen on self-renewal and differentiation of embryonic stem cells. Curr Opin Organ Transplant. Dec. 2009;14(6):694-700.

Mondragon-Teran et al., Lowering oxygen tension enhances the differentiation of mouse embryonic stem cells into neuronal cells. Biotechnol Prog. Sep.-Oct. 2009;25(5):1480-8.

Niebruegge et al., Generation of human embryonic stem cell-derived mesoderm and cardiac cells using size-specified aggregates in an oxygen-controlled bioreactor. Biotechnol Bioeng. Feb. 1, 2009;102(2):493-507.

Nir et al., Human embryonic stem cells for cardiovascular repair. Cardiovasc Res. May 1, 2003;58(2):313-23.

Okazaki et al., Oxygen, epigenetics and stem cell fate. Regen Med. Jan. 2006;1(1):71-83.

Papas et al., High-density culture of human islets on top of silicone rubber membranes. Transplant Proc. Oct. 2005;37(8):3412-4.

Pei, Regulation of pluripotency and reprogramming by transcription factors. J Biol Chem. Feb. 6, 2009;284(6):3365-9. Epub Sep. 26, 2008.

Pera et al., Regulation of human embryonic stem cell differentiation by BMP-2 and its antagonist noggin. J Cell Sci. Mar. 1, 2004;117(Pt 7):1269-80.

Powers et al., Effects of oxygen on mouse embryonic stem cell growth, phenotype retention, and cellular energetics. Biotechnol Bioeng. Oct. 1, 2008;101(2):241-54.

Przyborski, Differentiation of human embryonic stem cells after transplantation in immune-deficient mice. Stem Cells. Oct. 2005;23(9):1242-50.

Purpura et al., Soluble Flt-1 regulates Flk-1 activation to control hematopoietic and endothelial development in an oxygen-responsive manner. Stem Cells. Nov. 2008;26(11):2832-42. Epub Sep. 4, 2008.

Rambhatla et al., Generation of hepatocyte-like cells from human embryonic stem cells. Cell Transplant. 2003;12(1):1-11.

Ramirez et al., Effect of Oxygen tension and substrate on growth and differentiation of mouse embryonic stem cells. Reprod Fertil Dev. 2006;18(2):209-10.

Ramírez-Bergeron et al., Hypoxia affects mesoderm and enhances hemangioblast specification during early development. Development. Sep. 2004;131(18):4623-34.

Ramírez-Bergeron et al., Hypoxia-inducible factor and the development of stem cells of the cardiovascular system. Stem Cells. 2001;19(4):279-86.

Sato et al., Maintenance of pluripotency in human and mouse embryonic stem cells through activation of Wnt signaling by a pharmacological GSK-3-specific inhibitor. Nat Med. Jan. 2004;10(1):55-63. Epub Dec. 21, 2003.

Schwartz et al., Defined conditions for development of functional hepatic cells from human embryonic stem cells. Stem Cells Dev. Dec. 2005;14(6):643-55.

Semenza et al., Regulation of cardiovascular development and physiology by hypoxia-inducible factor 1. Ann N Y Acad Sci. Jun. 30, 1999;874:262-8.

Shih et al., Human embryonic stem cells are prone to generate primitive, undifferentiated tumors in engrafted human fetal tissues in severe combined immunodeficient mice. Stem Cells Dev. Dec. 2007;16(6):893-902.

Shirahashi et al., Differentiation of human and mouse embryonic stem cells along a hepatocyte lineage. Cell Transplant. 2004;13(3):197-211.

Silván et al., Hypoxia and pluripotency in embryonic and embryonal carcinoma stem cell biology. Differentiation. Sep.-Oct. 2009;78(2-3):159-68. Epub Jul. 14, 2009.

Soto-Gutierrez et al., Differentiation of human embryonic stem cells to hepatocytes using deleted variant of HGF and poly-aminourethane-coated nonwoven polytetrafluoroethylene fabric. Cell Transplant. 2006;15(4):335-41.

Spagnoli et al., Guiding embryonic stem cells towards differentiation: lessons from molecular embryology. Curr Opin Genet Dev. Oct. 2006;16(5):469-75. Epub Aug. 17, 2006.

Tian et al., Hematopoietic engraftment of human embryonic stem cell-derived cells is regulated by recipient innate immunity. Stem Cells. May 2006;24(5):1370-80. Epub Feb. 2, 2006.

Twork et al., Sensors in Bioprocess Conrol. CRC Press. May 25, 1990. p. 263. Retrieved from https://books.google.com/books?hl=en&h-=&id=9tsUypi4uP4C&oi=fnd&pg=PR3&dq=Twork,+C RC+Press+(1990).+Sensors+in+Bioprocess+Control&ots=PiBP61Bbtg&sig=w10_90FpYiUc-P6XQrNB86fcYBo#v=onepage&q=263Twork%2C%2OCRC%20Press%20(1990).%20Sensors%20in%20Bioprocess%20Control&f=false. 1 page.

West et al., In vitro gametogenesis from embryonic stem cells. Curr Opin Cell Biol. Dec. 2004;16(6):688-92.

Wion et al., $pO_2$ matters in stem cell culture. Cell Stem Cell. Sep. 4, 2009;5(3):242-3.

Wolff et al., Microelectrode measurements of pericellular $pO_2$ in erythropoietin-producing human hepatoma cell cultures. Am J Physiol. Nov. 1993;265(5 Pt 1):C1266-70.

Xu et al., Basic FGF and suppression of BMP signaling sustain undifferentiated proliferation of human ES cells. Nat Methods. Mar. 2005;2(3):185-90. Epub Feb. 17, 2005.

Xu et al., BMP4 initiates human embryonic stem cell differentiation to trophoblast. Nat Biotechnol. Dec. 2002;20(12):1261-4. Epub Nov. 11, 2002.

Yoon et al., Enhanced differentiation of human embryonic stem cells into cardiomyocytes by combining hanging drop culture and 5-azacytidine treatment. Differentiation. Apr. 2006;74(4):149-59. Erratum in: Differentiation. Jul. 2006;74(6):322.

Yoshida et al., Hypoxia enhances the generation of induced pluripotent stem cells. Cell Stem Cell. Sep. 2009 ;5(3):237-41. Epub Aug. 27, 2009.

Zhou et al., A gene regulatory network in mouse embryonic stem cells. Proc Natl Acad Sci U S A. Oct. 16, 2007;104(42):16438-43. Epub Oct. 10, 2007.

Abaci et al., Adaptation to oxygen deprivation in cultures of human pluripotent stem cells, endothelial progenitor cells, and umbilical vein endothelial cells. Am J Physiol Cell Physiol. Jun. 2010;298(6):C1527-37. doi: 10.1152/ajpcell.00484.2009. Epub Feb. 24, 2010.

Abbasalizadeh et al., Bioprocess development for mass production of size-controlled human pluripotent stem cell aggregates in stirred

(56) References Cited

OTHER PUBLICATIONS suspension bioreactor. Tissue Eng Part C Methods. Nov. 2012;18(11):831-51. doi: 10.1089/ten.TEC.2012.0161. Epub Jun. 13, 2012. Abstract Only.

Bonakdar et al., Preparation and Characterization of polyvinyl alcohol hydrogels crosslinked by biodegradable polyurethane for tissue engineering of cartilage. Mater Sci Eng C. Feb. 2010;30:636-43.

Cheng et al., Self-renewing endodermal progenitor lines generated from human pluripotent stem cells. Cell Stem Cell. Apr. 6, 2012;10(4):371-84. doi: 10.1016/j.stem.2012.02.024. With Supplemental Information.

Gordon et al., Role of transforming growth factor-beta superfamily signaling pathways in human disease. Biochim Biophys Acta. Apr. 2008;1782(4):197-228. Doi: 10.1016/j.bbadis.2008.01.006. Epub Feb. 11, 2008.

Green et al., Generation of anterior foregut endoderm from human embryonic and induced pluripotent stem cells. Nat Biotechnol. Mar. 2011;29(3):267-72 plus online methods. Doi: 10.1038/nbt.1788. Epub Feb. 27, 2011.

Hamon et al., Direct oxygen supply with polydimethylsiloxane (PDMS) membranes induces a spontaneous organization of thick heterogeneous liver tissues from rat fetal liver cells in vitro. Cell Transplant. 2012;21(2-3):401-10. Doi: 10.3727/096368911X605303.

Kobayashi et al., Corneal cell adhesion and proliferation on hydrogel sheets bound with cell-adhesive proteins. Curr Eye Res. 1991;10(10):899-908.

Mei et al., Combinatorial development of biomaterials for clonal growth of human pluripotent stem cells. Nat Mater. Sep. 2010;9(9):768-78. Doi: 10.1038/nmat2812. Epub Jul. 3, 2012. 22 pages.

Nostro et al., Stage-specific signaling through TGFβ family members and WNT regulates patterning and pancreatic specification of human pluripotent stem cells. Development. Mar. 2011;138(5):861-71. Doi: 10.1242/dev.055236. Epub Jan. 26, 2011. Erratum in: Development. Mar. 2011;138(5).doi: 10.1242/dev.065904. Development. Apr. 2011;138(7):1445.

Powers et al., Accurate control of oxygen level in cells during culture on silicone rubber membranes with application to stem cell differentiation. Biotechnol Prog. May-Jun. 2010;26(3):805-18. doi: 10.1002/btpr.359.

Simoni et al., Retinoic acid and analogs as potent inducers of differentiation and apoptosis. New promising chemopreventive and chemotherapeutic agents in oncology. Pure Appl Chem. 2001;73(9):1437-1444.

Volkmer et al., Hypoxia in static and dynamic 3D culture systems for tissue engineering of bone. Tissue Eng Part A. Aug. 2008;14(8):1331-40. doi: 10.1089/ten.tea.2007.0231.

\* cited by examiner

US 9,447,378 B2

METHOD FOR DIFFERENTIATING HUMAN EMBRYONIC STEM CELLS INTO β-CELLS FOR THE TREATMENT OF TYPE I DIABETES

RELATED APPLICATIONS

This application claims benefit and priority under 35 U.S.C. §119(e) to U.S. Provisional Application Ser. No. 61/639,794, entitled "METHOD FOR DIFFERENTIATING HUMAN EMBRYONIC STEM CELLS (HES) INTO β-CELLS FOR THE TREATMENT OF TYPE I DIABETES" filed on Apr. 27, 2012, which is herein incorporated by reference in its entirety.

FEDERALLY SPONSORED RESEARCH

This invention was made with U.S. Government support under RC1 DE020761 awarded by the NIH. The U.S. Government has certain rights in the invention.

BACKGROUND OF INVENTION

Pluripotent stem cells (PSC) hold promise for cell replacement therapy and studying embryonic development. Most PSC research is performed in high, non-physiological $O_2$.

SUMMARY OF INVENTION

The invention is based in part on the results of a study showing that physiological $O_2$ markedly influences differentiation to insulin-producing cells. In these experiments, as described in greater detail herein, human embryonic stem cells (hESC) were differentiated under different $pO_2$ environments by controlling cellular oxygen exposure through adhesion culture on highly $O_2$-permeable silicone rubber membranes. The differentiation of hESC was focused to c-peptide+ cells using an improved modification of a previously described 5-stage protocol (D'Amour et al., *Nat. Biotechnol.* 24, 1393-1401 (2006)). It was found, in accordance with the invention, that differentiation under 5% $O_2$ from hESC to definitive endoderm (stage 1), primitive gut tube (stage 2), and posterior foregut (stage 3), followed by 20% $O_2$ to pancreatic endoderm (stage 4) and insulin-producing cells (stage 5) gives rise to a cell population that is 25% positive for both c-peptide and insulin. This result was 5 times greater than the result obtained by differentiation under normoxic conditions (20% $O_2$). The cells cultured under hypoxia passively secreted c-peptide into the medium but were not glucose responsive. All pancreatic endoderm genetic markers were increased for the controlled-hypoxia (5% stage 1-3, 20% stage 4-5) when compared to the normoxic condition (20% stage 1-5). By examining each stage at multiple controlled high and low oxygen levels, we identified $O_2$ conditions that increased the fraction of the intermediate cell type of each cell measured by flow cytometry, or increased expression of genetic markers for those intermediate stages measured by real-time PCR. By combining these oxygen levels appropriately, we achieved a large improvement. Preliminary results on stage 4 cells have indicated potential $O_2$ conditions that result in a 50% c-peptide+ population. Based on these results $O_2$ combined with other directed differentiation protocols is a potentially-straightforward method that could be applied to future cell therapy protocols to generate more of a desired cell type.

Thus, in one aspect, the invention provides a method comprising differentiating embryonic stem cells to posterior foregut endoderm in vitro, at low oxygen partial pressure ($pO_2$), and differentiating posterior foregut endoderm to insulin+ and/or C-peptide+ cells in vitro, at higher $pO_2$.

In another aspect, the invention provides a method comprising differentiating human embryonic stem cells to a definitive endoderm stage at low oxygen partial pressure ($pO_2$). The method may further comprise differentiating the definitive endoderm stage to a primitive gut tube stage at low oxygen partial pressure ($pO_2$). The method may further comprise differentiating the primitive gut tube stage to a posterior foregut stage at low oxygen partial pressure ($pO_2$). The method may further comprise differentiating the posterior foregut stage to a pancreatic endoderm stage at an increased oxygen partial pressure ($pO_2$). The method may further comprise differentiating the pancreatic endoderm stage to an insulin+ and/or C-peptide+ cell stage at an increased oxygen partial pressure ($pO_2$).

In another aspect, the invention provides a method comprising differentiating human embryonic stem cells to a definitive endoderm stage in vitro at low oxygen partial pressure ($pO_2$).

In another aspect, the invention provides a method comprising differentiating definitive endoderm to primitive gut tube in vitro at low oxygen partial pressure ($pO_2$).

In another aspect, the invention provides a method comprising differentiating primitive gut tube to posterior foregut in vitro at low oxygen partial pressure ($pO_2$).

In another aspect, the invention provides a method comprising differentiating posterior foregut to pancreatic endoderm in vitro at an increased oxygen partial pressure ($pO_2$).

In another aspect, the invention provides a method comprising differentiating pancreatic endoderm into insulin+ and/or C-peptide+ cells in vitro at an increased oxygen partial pressure ($pO_2$).

In some embodiments, the embryonic stem cells are differentiated on an oxygen permeable membrane. In some embodiments, one or more, including all, of the differentiation methods are performed on an oxygen permeable membrane. In some embodiments, the oxygen permeable membrane is an oxygen permeable silicone rubber membrane. In some embodiments, the oxygen permeable silicone rubber membrane is coated with extracellular matrix (ECM). In some embodiments, the low oxygen partial pressure ($pO_2$) is 36 mmHg. In some embodiments, the higher or increased oxygen partial pressure ($pO_2$) is 142 mmHg.

In some embodiments, the embryonic stem cells are human embryonic stem cells.

In another aspect, the invention provides a composition comprising a population of in vitro cultured cells wherein at least 30% of the cells are insulin+ and/or C-peptide+. In some embodiments, about 50% of the cells are insulin+ and/or C-peptide+.

Each of the limitations of the invention can encompass various embodiments of the invention. It is therefore anticipated that each of the limitations of the invention involving any one element or combinations of elements can be included in each aspect of the invention. This invention is not limited in its application to the details of construction and/or the arrangement of components set forth in the following description or illustrated in the Figures. The invention is capable of other embodiments and of being practiced or of being carried out in various ways.

The phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

DETAILED DESCRIPTION OF INVENTION

Figure 1:
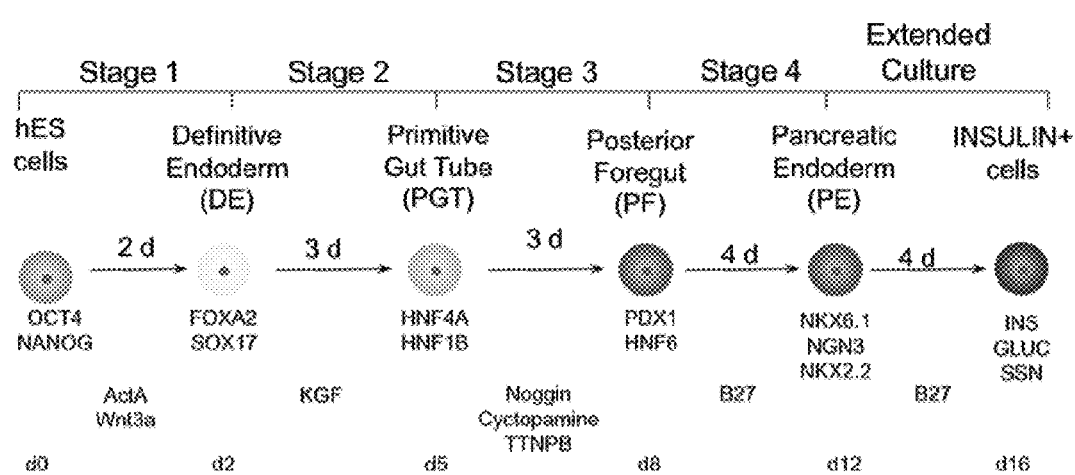
FIG. 1. Summary of culture conditions for the multi-stage differentiation protocol generally. As an example, CyT49 hES cells were used as the starting cell population. Successive rows identify stage number, primary tissue expected (and its abbreviations), number of days between stages, transcription factors measured by qPCR, major additives at each stage, and the accumulation of time.

This invention relates to a novel method for differentiating embryonic stem (ES) cells, including human embryonic stem (hES) cells, into β-cells for the treatment of Type I Diabetes. These methods use partial pressure of oxygen ($pO_2$) experienced by ES cells in order to modulate and direct differentiation of these immature cells. Preliminary studies with mouse ES (mES) cells demonstrate that accurate control of $pO_2$ at hypoxic levels dramatically changes timing and magnitude of differentiation markers and enhances differentiation to mesodermal and endodermal but not ectodermal lineages. It has been found that differentiation of hES cells from one stage of endodermal derivatives to the next is enhanced by low $pO_2$ culture. In some embodiments, ECM-coated silicone rubber membranes having high oxygen permeability are used as a culture substrate so that the $pO_2$ to which the cells are exposed ($pO_{2cell}$) is the same as the gas phase ($pO_{2gas}$).

The invention is based in part on the finding that variation of $O_2$ in a controlled manner markedly enhances multi-stage differentiation of embryonic stem cells to insulin-producing cells. As described in greater detail herein, hES cells (e.g., CyT49) were differentiated using a modification of a 5-stage protocol of D'Amour et. al. (*Nat. Biotechnol.* 24, 1393-1401 (2006); and Kroon et al., *Nature Biotechnol.* 26, 443-452 (2008), the entire contents of both of which are incorporated by reference herein) under different sequences of well-characterized $pO_2$ environments. Cellular oxygen exposure was controlled through adhesion culture on highly $O_2$-permeable silicone rubber membranes so that the cells in contact with the membrane were exposed to the same $pO_2$ as in the gas phase of the culture.

The inventors hypothesized that effects of low $O_2$ on the early stages of differentiation can be manifested in later stages of differentiation. Each stage comprised two steps. We started with stage 1 at six different $O_2$ levels (1%, 3%, 5%, 8%, 10%, & 20%). Samples at the end of stage 1 were analyzed with qPCR and flow cytometry for markers of definitive endoderm (DE). In the second step, the differentiation was carried to completion. The three oxygen levels that produced the highest fraction of DE cells were then used in stage 1, and the remaining stages were carried out at 20% $O_2$. Each set of complete differentiation experiments employed a control condition of constant 20% $O_2$ for comparison. The best stage 1 $O_2$ level was selected on the basis of the fraction c-peptide+ and/or insulin+ cells in the stage 5 preparation as well as the extent of gene expression of relevant pancreatic endoderm (PE) and beta cell markers, and this $O_2$ level was used for all subsequent experiments. This two-step process was repeated sequentially with stages 2, 3, and 4; the condition for stage 5 was fixed at 20% $O_2$. Beginning with stage 3 an additional $O_2$ condition of 40% was added to the conditions tested. Altogether, 12 different sequences of $O_2$ levels in successive stages were evaluated. The approach and the results obtained are described in greater detail below.

A systematic plan was developed that was workable with available resources to evaluate the effect of reduced $pO_{2gas}$ using the protocol of D'Amour et al. (*Nat. Biotechnol.* 24, 1393-1401 (2006)) (FIG. 1). It was based on the hypothesis that (1) the early stages of pancreas formation likely occur at physiologically at reduced $pO_2$, and only later stages, perhaps only stage 4, require higher $pO_2$; and (2) the multi-stage protocol represents a cascading sequence of events and it is possible that small effect observed at stage 1 would be amplified by stage 4.

Figure 2:
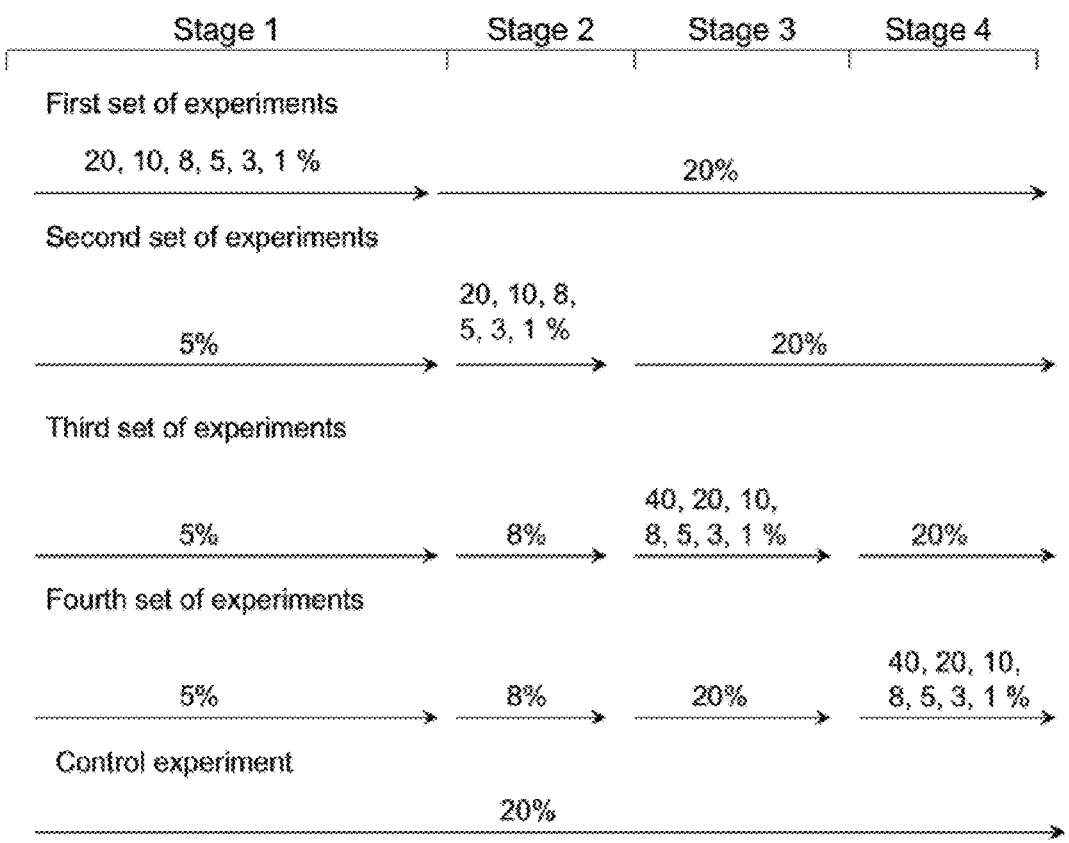
FIG. 2. One example for sets of experiments to systematically investigate reduced $pO_2$ effects on differentiation. Numbers represent percent oxygen, which correspond (from low to high) to $pO_{2gas}$ values of 7, 21, 36, 57, 71, 142, and 285 mmHg.

FIG. 2 illustrates how this strategy was carried out. In the first set of experiments starting at stage 1, six different $pO_{2gas}$ levels were investigated with all subsequent stages at 142 mmHg. In the second set, the most promising value(s) were selected for stage 1, and all six $pO_{2gas}$ would be evaluated at stage 2. The high $pO_{2gas}$, 142 mmHg, control would be repeated in each set. Markers are analyzed by qPRC and other assays at each stage. After four sets of experiments, we would have the optimum profile of $pO_{2gas}$ at each stage.

Figure 3:
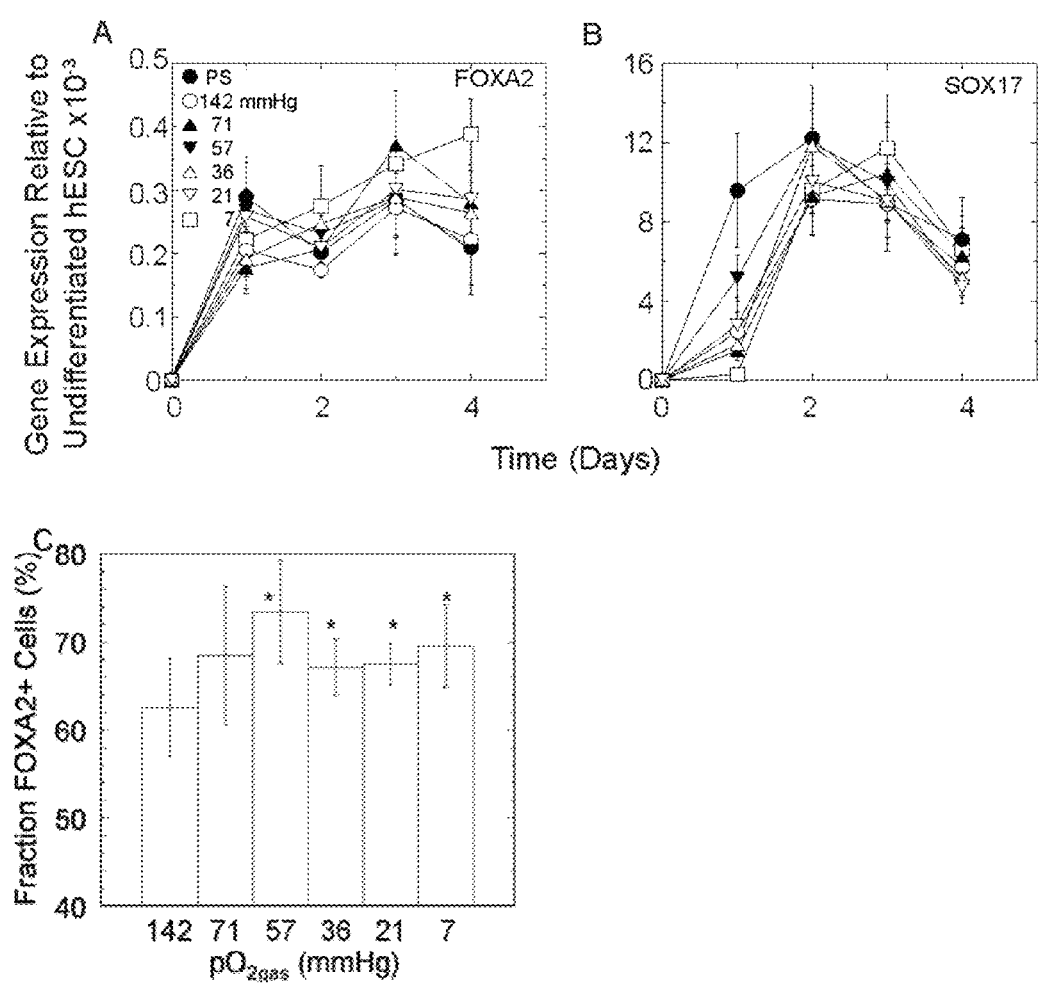
FIG. 3. Measurements of FOXA2 (A, C) and SOX17 (B) for CyT49 hESC differentiated during stage 1 at six different $pO_{2gas}$ ranging from 142 to 7 mmHg. Gene expression of FOXA2(A) and SOX17 (B) measured by qPCR. Fraction of FOXA2+ cells (C) measured by flow cytometry. Asterisk represents a p-value less than 0.05 when samples compared to 142 mmHg. Data are presented as mean±standard deviation of six independent samples.
Figure 4:
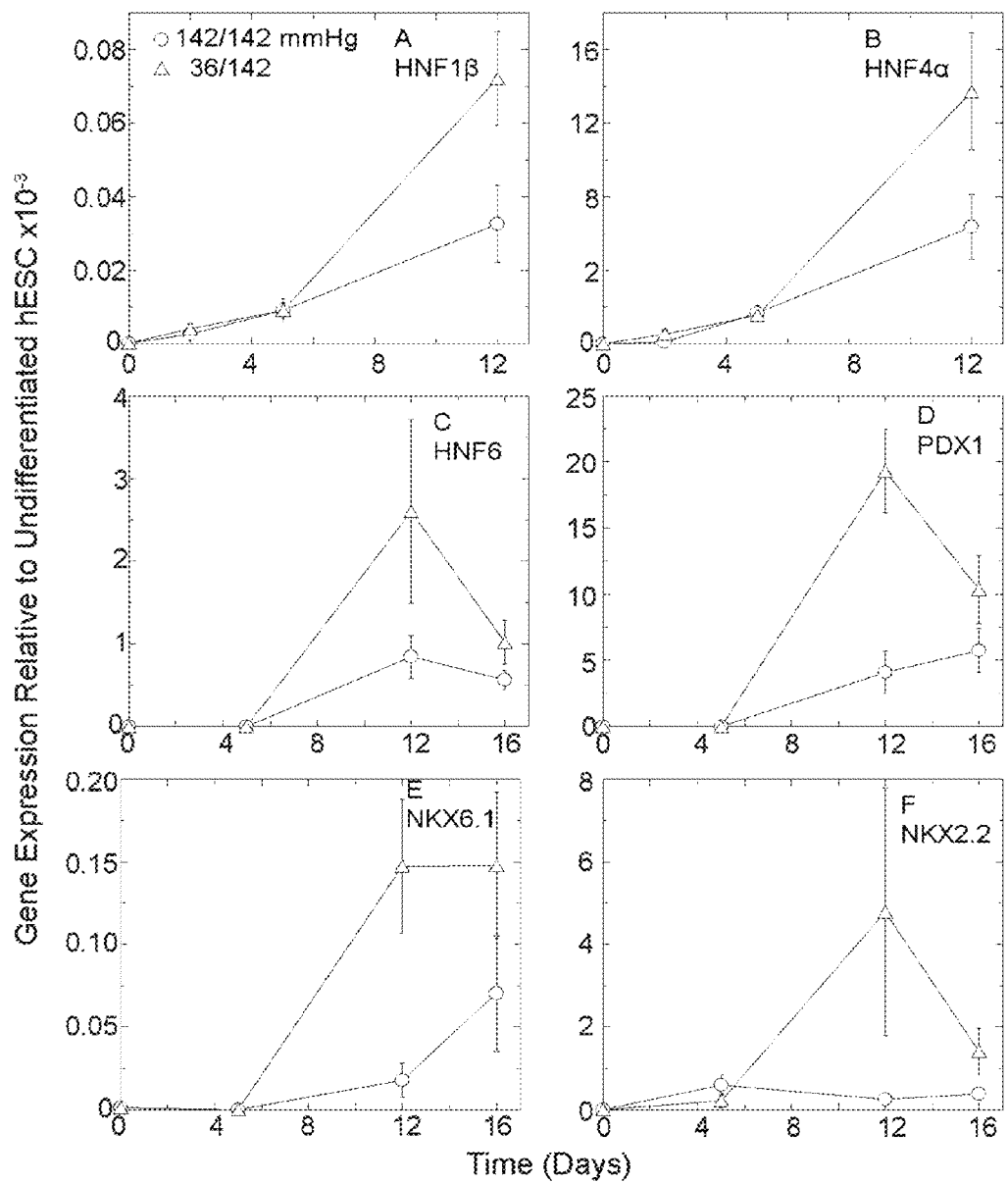
FIG. 4. Gene expression of the PFG markers (A) HNF1β and (B) HNF4α, PF markers HNF6 (C) and PDX1 (D), and PE markers NKX6.1 (E) and NKX2.2 (F). CyT49 hESC differentiated during stage 1 at 142 mmHg (open circle) or 36 mmHg (open triangle). Data are presented as mean±standard deviation of six independent samples.
Figure 5:
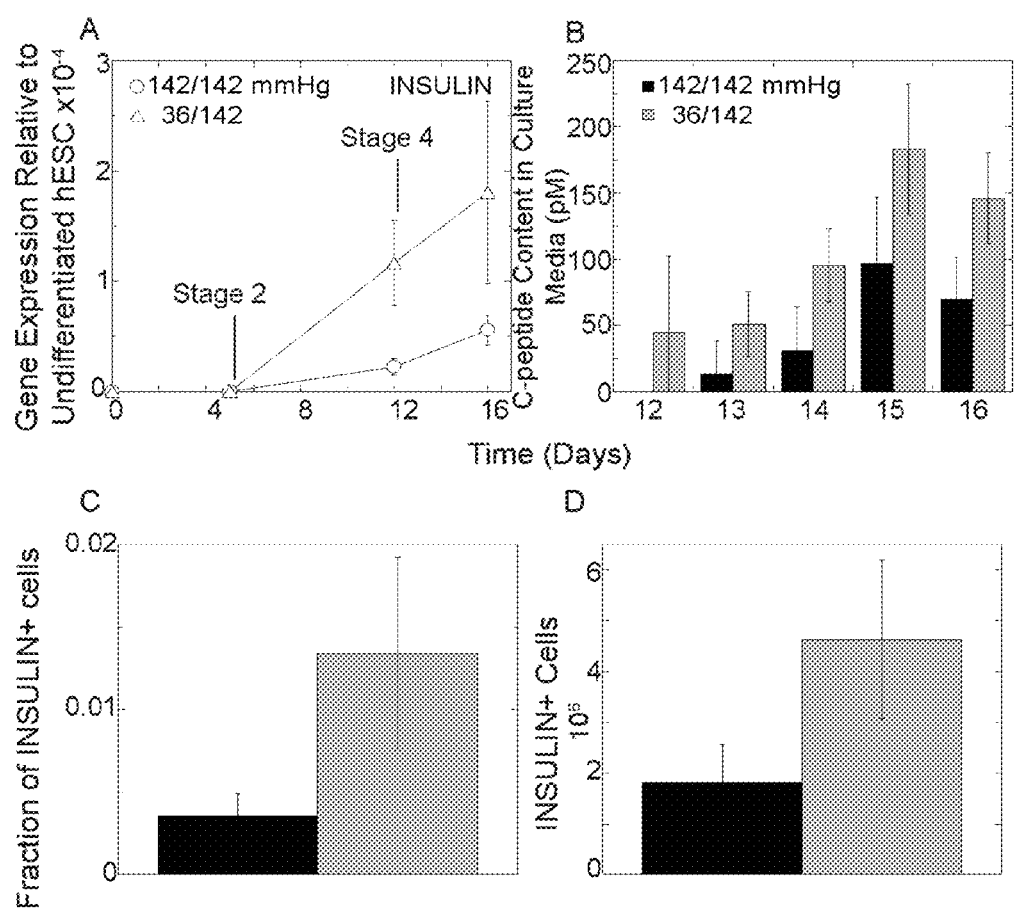
FIG. 5. Measurements of INSULIN for CyT49 hESC differentiated during stage 1 at either 142 or 36 mmHg then differentiated to subsequent stages at 142 mmHg. (A) Gene expression of the INSULIN measured by qPCR. (B) Concentration of C-peptide in the culture media measured by ELISA. (C) Fraction of INSULIN+ cells measured by flow cytometry. (D) Number of INSULIN+ cells. The notation 142/142 refers to cells differentiated entirely at 142 mmHg and 36/142 refers to cells differentiated during stage 1 at 36 then at 142 for the remainder of the protocol. Data are presented as mean±standard deviation of six independent samples.
Figure 6:
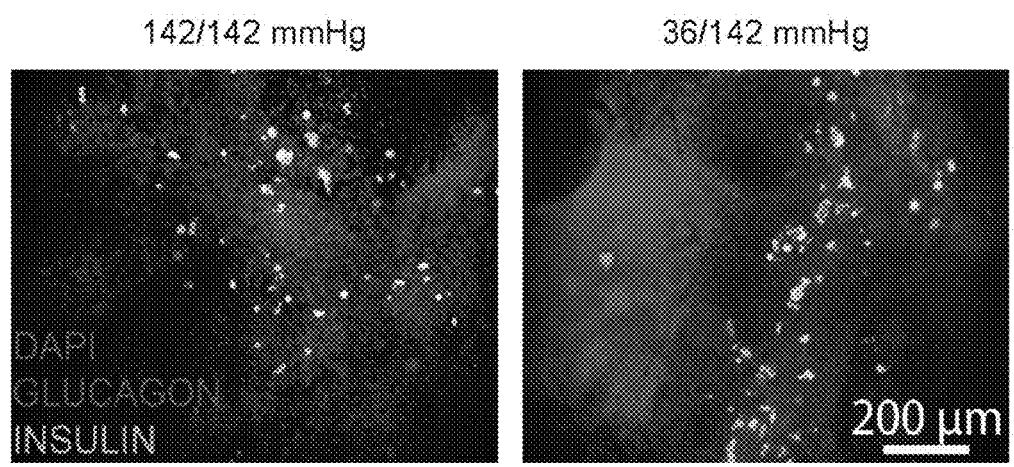
FIG. 6. En face images of CyT49 hESC differentiated 16 days on stained with DAPI, anti-GLUCAGON antibody, and anti-INSULIN antibody.

At stage 1, we observed a small but statistically significant increase in the fraction of Foxa2+ cells, from 60% at 142 mmHg to 70% at 7-57 mmHg measured with flow cytometry, and in gene expression of FOXA2 and SOX17 measured with qPCR (FIG. 3). Cells differentiated 2 days at 142 or 36 mmHg to produce definitive endoderm (DE) were then further differentiate with the multi-stage protocol at 142 mmHg $pO_{2gas}$ to stages 2, 3, and 4 and to day 16 to produce Insulin+ cells. This created two cases, one in which cells were differentiated 16 days entirely at 142 mmHg $pO_{2gas}$ and a second in which cells were differentiated 2 days at 36 mmHg $pO_{2gas}$ and the subsequent 14 days at 142 mmHg $pO_{2gas}$. Expression of the stage 2 markers HNF1β and HNF4α, measured with qPCR, was the same on day 5 for the two cases but was a factor of 2 higher on day 12 at 36 mmHg compared to 142 mmHg $pO_{2gas}$ (FIGS. 4A, B). Stage 1 differentiation at 36 mmHg increased expression of the posterior foregut (PF) and pancreatic endoderm (PE) markers HNF6, PDX1, NKX6.1 and NKX2.2, measured with qPCR, by factors of 10, 2, 8, and 18, respectively, compared to 142 mmHg on day 12 (FIGS. 4C-F). Insulin expression, measured with qPCR, was a factor of 3 higher for 36 mmHg compared to the 142 mmHg on day 16. C-peptide in the culture medium, measured with ELISA, was first detected on day 12 at 36 mmHg compared to day 13 at 142 mmHg (FIG. 5). C-peptide concentration was a factor of 2 higher from day 13 through day 16 for the low compared to high $pO_{2gas}$ conditions, which correlated with a factor of 2 increase in the fraction of Insulin+ cells measured with flow cytometry. With immunocytochemistry, we observed that many cells that were Insulin+ were also Glucagon+ (FIG. 6). The data indicate that culture at 36 mmHg $pO_{2gas}$ during the first stage of differentiation produces improved results of all stages. The very large effects of reduced $pO_{2gas}$ culture for stage 1 that became apparent only at later stages indicates that there are long-lasting effects of reduced $pO_{2gas}$ that are not being picked up by current assays.

Figure 7:
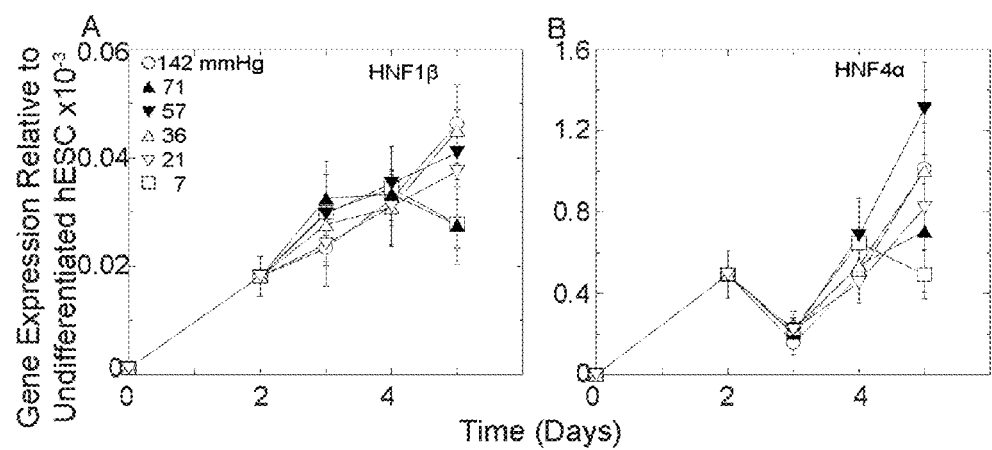
FIG. 7. Gene expression of the PFG markers (A) HNF1β and (B) HNF4α. CyT49 hESC differentiated during stage 2 six different $pO_{2gas}$ ranging from 142 to 7 mmHg. Data are presented as mean±standard deviation of six independent samples.

We performed stage 1 differentiation at 36 mmHg and then stage 2 differentiation at 142, 71, 57, 36, 21, and 7 mmHg $pO_{2gas}$ Gene expression of HNF1β and HNF4α (PGT markers) was highest at 142, 57, and 36 mmHg and lowest at 7 mmHg (FIG. 7). HNF1β expression was a factor of 1.6, 1.5, and 1.5 higher and HNF4α expression a factor of 2.0, 2.7, and 2.0 higher at 142, 57, and 36 mmHg, respectively, compared to 7 mmHg.

We further investigated this finding by assessing the potential of high and low $pO_{2gas}$-derived PGT to form all subsequent cell types: PF (stage 3), PE (stage 4) and insulin-expressing cells (stage 5). Specifically, we performed the complete differentiation protocol to produce Insulin+ cells, assessing differentiation to each intermediate stage, using four combinations of $pO_{2gas}$ (Stage 1/2/3/4):

(1) 36/142/142/142 mmHg
(2) 36/57/142/142 mmHg
(3) 36/36/142/142 mmHg
(4) 142/142/142/142 mmHg, acting as a control.

Figure 8:
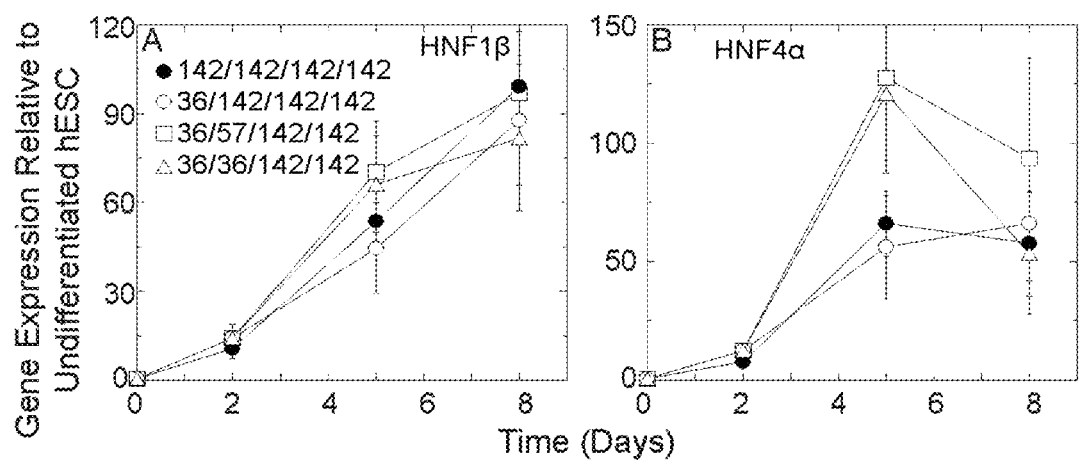
FIG. 8. Gene expression of the PGT markers (A) HNF1β and (B) HNF4α. CyT49 hESC were differentiated during stage 1/2/3/4 at 36/142/142/142 mmHg (open circle), 36/57/142/142 mmHg (open square), 36/36/142/142 mmHg (open triangle) or 142/142/142/142 mmHg (closed circle, control condition). Data are presented as mean±standard deviation of six independent samples.
Figure 9:
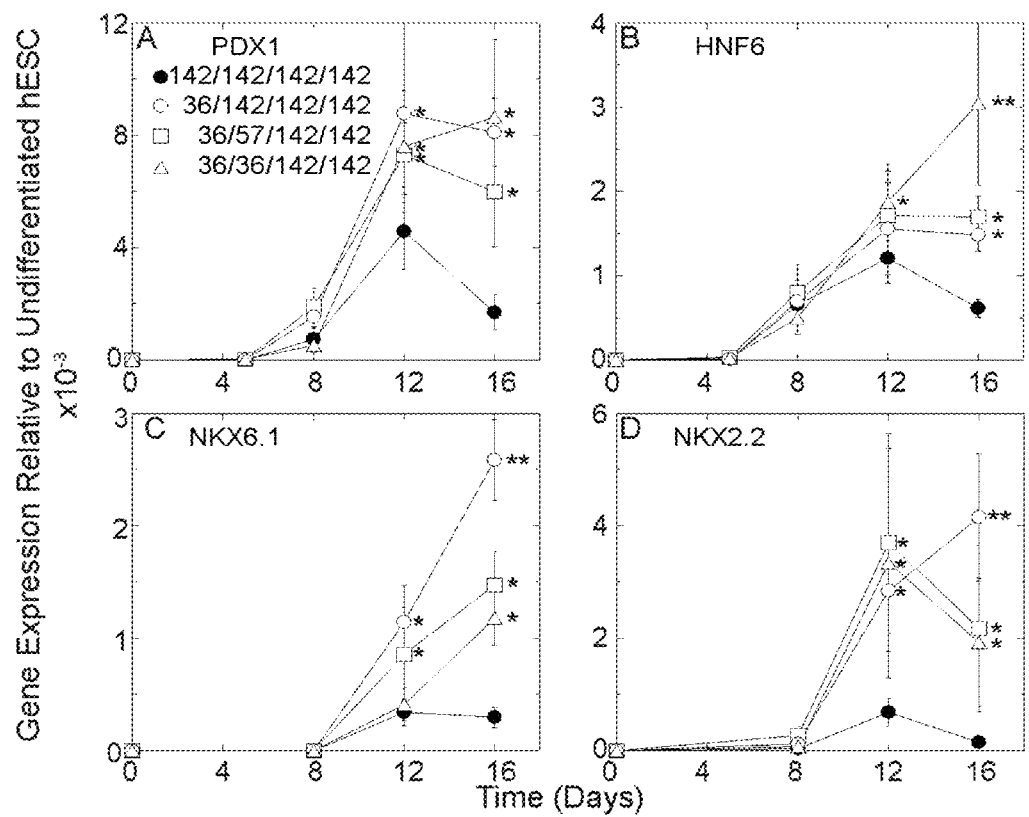
FIG. 9. Gene expression of the PF markers PDX1 (A) and HNF6 (B), and PE markers NKX6.1 (C) and NKX2.2 (D). CyT49 hESC were differentiated during stage 1/2/3/4 at 36/142/142/142 mmHg (open circle), 36/57/142/142 mmHg (open square), 36/36/142/142 mmHg (open triangle) or 142/142/142/142 mmHg (closed circle, control condition). Asterisk (*) represents statistical significance when compared with the control condition at the given time point (ttest, p<0.03). Double asterisk (**) represents statistical significance when compared to all conditions at the given time point (ttest, p<0.03). Data are presented as mean±standard deviation of six independent samples.
Figure 10:
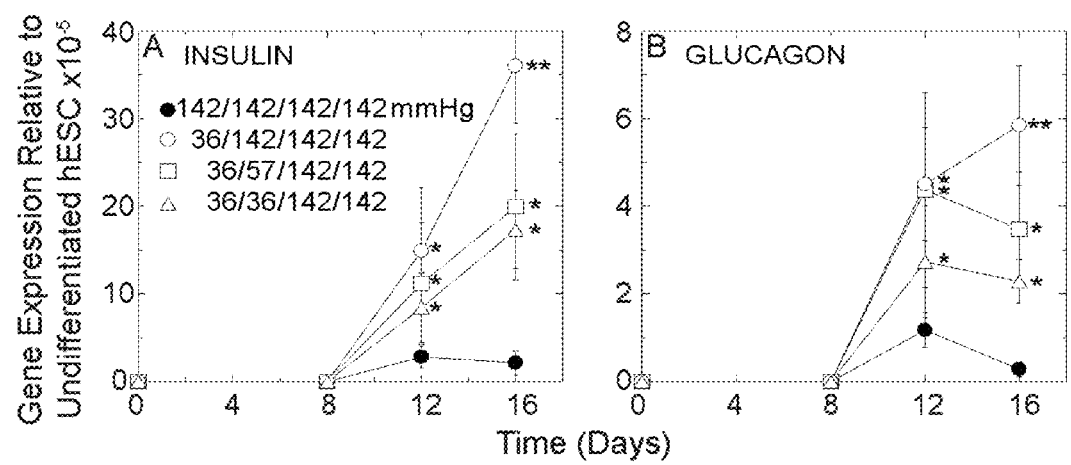
FIG. 10. Gene expression of the INSULIN (A) and GLUCAGON (B). CyT49 hESC were differentiated during stage 1/2/3/4 at 36/142/142/142 mmHg (open circle), 36/57/142/142 mmHg (open square), 36/36/142/142 mmHg (open triangle) or 142/142/142/142 mmHg (closed circle, control condition). Asterisk (*) represents statistical significance when compared with the control condition at the given time point (ttest, p<0.03). Double asterisk (**) represents statistical significance when compared to all conditions at the given time point (ttest, p<0.03). Data are presented as mean±standard deviation of six independent samples.
Figure 11:
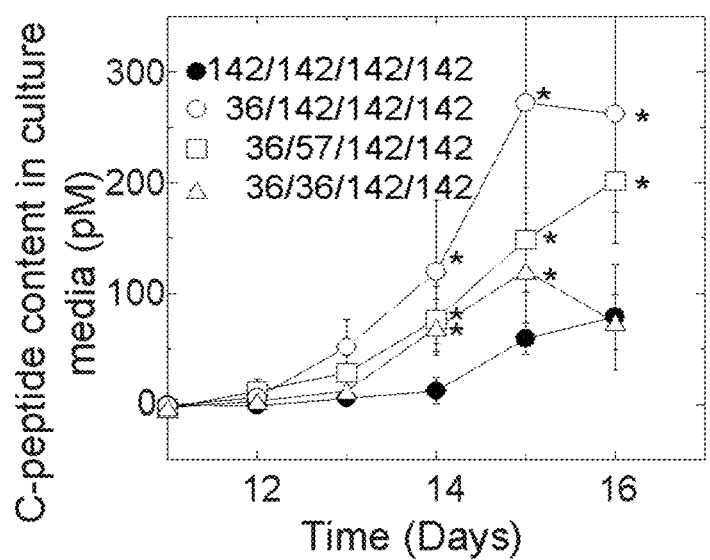
FIG. 11. Measurements of C-peptide content in culture media for CyT49 hESC CyT49 hESC were differentiated during stage 1/2/3/4 at 36/142/142/142 mmHg (open circle), 36/57/142/142 mmHg (open square), 36/36/142/142 mmHg (open triangle) or 142/142/142/142 mmHg (closed circle, control condition). Asterisk (*) represents statistical significance when compared with the control condition at the given time point (ttest, p<0.03). Data are presented as mean±standard deviation of six independent samples.
Figure 12:
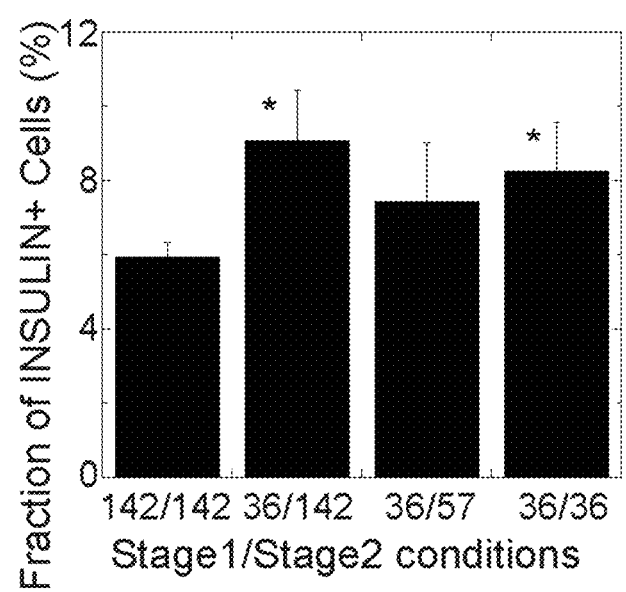
FIG. 12. Measurements of INSULIN+ cells at day 16 (stage 5). CyT49 hESC were differentiated during stage 1/2 at 36/142 mmHg, 36/57 mmHg, 36/36 mmHg, or 142/142 mmHg (control condition). Asterisk (*) represents statistical significance when compared with the control condition (ttest, p<0.03). Data are presented as mean±standard deviation of six independent samples.

Expression of the stage 2 markers HNF1β and HNF4α, measured with qPCR, was higher on day 5 for 36/36/142/142 and 36/57/142/142, but the differences were not statistically significant (FIG. 8). As the differentiation progressed to PF (stage 3), test conditions (case 1, 2, 3) were significantly higher than the control (case 4) but not from each other for the PF markers PDX1 and HNF6 (FIGS. 9A, B). A noticeable difference was observed with the PE markers NKX6.1 and NKX2.2, which are expressed during stage 4 and stage 5. During stage 2, differentiation at 36/142/142/142 mmHg $pO_{2gas}$ (case 1) resulted in a factor of 1.3 and 1.9 higher expression of NKX6.1 and NKX2.2, respectively, when compared to either 36/57/142/142 (case 2) or 36/36/142/142 mmHg (case 3) $pO_{2gas}$ (FIGS. 9C, D). Case 1 differentiation also resulted in a factor of 2 increase of Insulin and Glucagon gene expression when compared to case 2 and 3 differentiation conditions (FIG. 10). C-peptide in the culture medium, measured with ELISA, was first detected on day 12 for all but the control condition. While the c-peptide concentrations were statically different between cases 1-3 and the control, cases 1-3 were not statistically different from each other. Case 1-derived PGT always resulted in the highest amount of c-peptide released when compared to all cases (FIG. 11). All three cases resulted in more fraction Insulin+ cells, measured with flow cytometry (FIG. 12). With immunocytochemistry, we observed that many cells that were Insulin+ were also Glucagon+(data not shown). The data indicate that culture at 36 mmHg $pO_{2gas}$ during the first stage of differentiation followed by differentiation at 142 mmHg during stage 2 produces more Insulin+ cells, and the largest gene expression of PE markers and Insulin.

We further investigated how oxygen levels affect the differentiation from primitive gut tube (PGT, stage 2) to posterior foregut (PF, stage 3). For these experiments, stage 1 differentiation took place at 36 mmHg and stage 2 differentiation at 142 mmHg. Stage 3 culture took place at 285, 142, 71, 36, 21, and 7 mmHg $pO_{2gas}$. The high $pO_{2gas}$ (285 mmHg) was equivalent to humidified 40% $O_2$ and was added based on a hypothesis that high oxygen may become important during later stages of differentiation to β cells.

Figure 13:
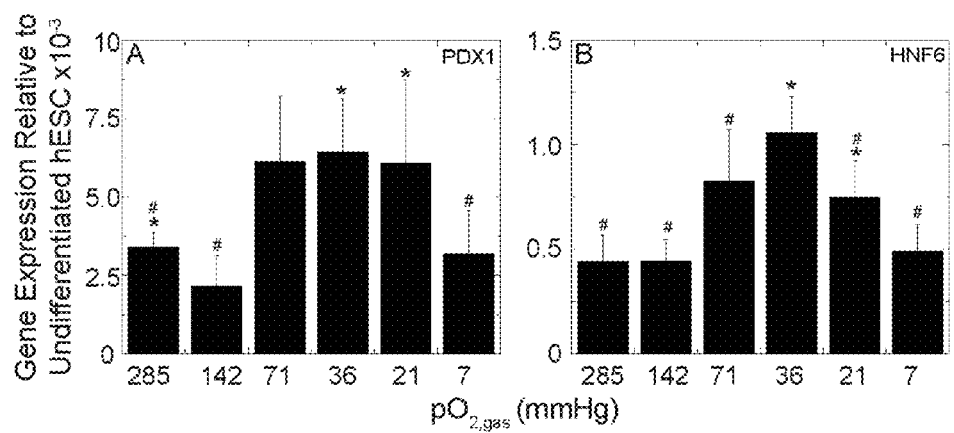
FIG. 13. Gene expression of the PF markers (A) PDX1 and (B) HNF6 on day 8. CyT49 hESC were differentiated during stage 1/2 at 36/142 mmHg, followed by stage 3 at 285, 142, 71, 36, 21 and 7 mmHg. Data are presented as mean±standard deviation of six independent samples. (*) represents a p value <0.05 when compared to 142 mmHg (t-test) and (#) represents a p value <0.05 when compared to 36 mmHg (t-test).
Figure 14:
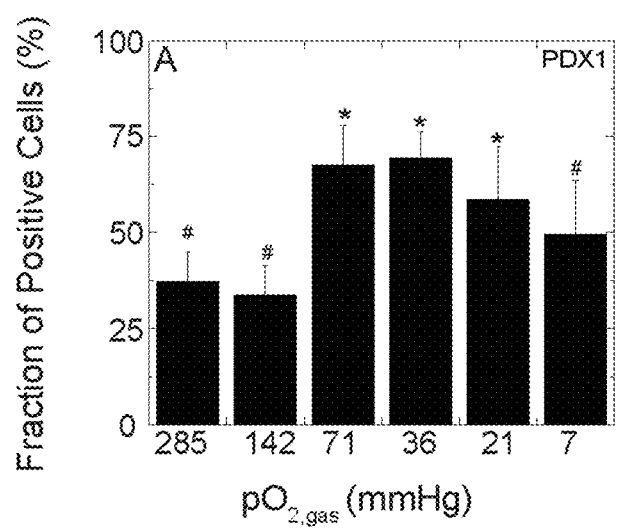
FIG. 14. Fraction of PDX1+ cells on day 8. CyT49 hESC were differentiated during stage 1/2 at 36/142 mmHg, followed by stage 3 at 285, 142, 71, 36, 21 and 7 mmHg. Data are presented as mean±standard deviation of six independent samples. (*) represents a p value <0.05 when compared to 142 mmHg (t-test) and (#) represents a p value <0.05 when compared to 36 mmHg (t-test).

We showed that low oxygen differentiation between 71 and 21 mmHg gave rise to the highest gene expression, measured by qPCR, of markers for PF, PDX1 and HNF6 (FIG. 13). Gene expression of PDX1 and HNF6 were a factor of 3 higher at 36 than at 142 mmHg. During this experiment, we were able to use flow cytometry to examine cells for PDX1. The fraction of PDX1 positive cells followed the same trend as gene expression data (FIG. 14). The fraction of PDX1+ cells was highest at 36 mmHg, followed by 71 and 21 mmHg. The worst cases were 285 and 142 mmHg with 7 mmHg falling between the two groups.

Based on gene expression of PDX1 and HNF6 and the percentage of PDX1+ cells, we identified 36 mmHg as a strong potential candidate for stage 3 differentiation. We investigated the following four cases to determine if differentiation at 36 mmHg during stage 3 will give rise to more PE and Insulin+ cells:

1. Stage 1 at 36 mmHg, Stage 2 at 142 mmHg, Stage 3 at 142 mmHg, and subsequent stages at 142 mmHg.
2. Stage 1 at 36 mmHg, Stage 2 at 142 mmHg, Stage 3 at 36 mmHg, and subsequent stages at 142 mmHg.
3. Stage 1 at 36 mmHg, Stage 2 at 36 mmHg, Stage 3 at 36 mmHg, and subsequent stages at 142 mmHg.
4. All stages at 142 mmHg, acting as a control.

Figure 15:
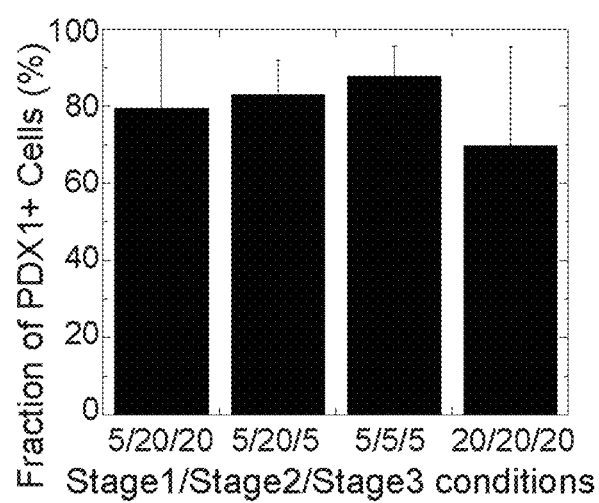
FIG. 15. Fraction of PDX1+ cells on day 8. CyT49 hESC were differentiated during stage 1/2/3 at the oxygen conditions shown and then stage 4 and 5 were performed at 20% oxygen. Data are presented as mean±standard deviation of six independent samples.
Figure 16:
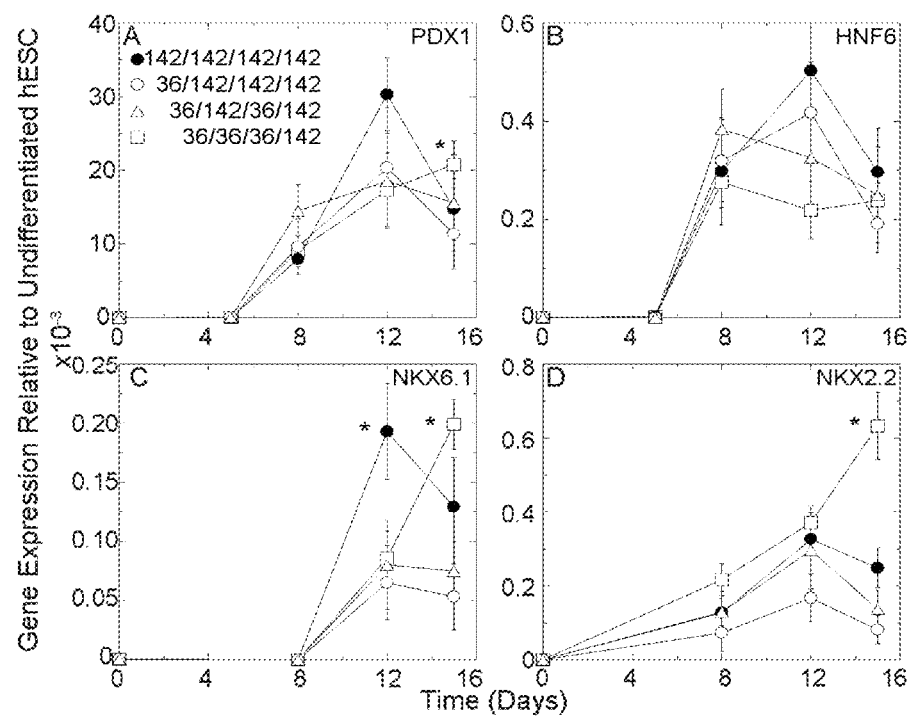
FIG. 16. Gene expression of the PF markers PDX1 (A) and HNF6 (B), and PE markers NKX6.1 (C) and NKX2.2 (D). CyT49 hESC were differentiated during stage 1/2/3/4 at 36/142/142/142 mmHg (open circle), 36/142/36/142 mmHg (open triangle), 36/36/36/142 mmHg (open triangle) or 142/142/142/142 mmHg (closed circle, control condition). Asterisk (*) represents statistical significance when compared to all conditions at the given time point (ttest, p<0.05). Data are presented as mean±standard deviation of six independent samples.
Figure 17:
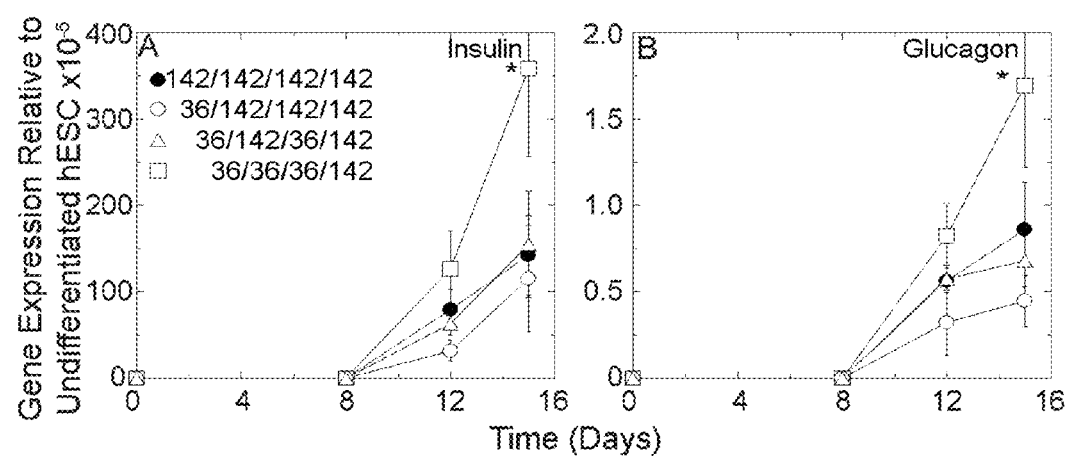
FIG. 17. Gene expression of the Insulin (A) and Glucagon (B). CyT49 hESC were differentiated during stage 1/2/3/4 at 36/142/142/142 mmHg (open circle), 36/142/36/142 mmHg (open triangle), 36/36/36/142 mmHg (open triangle) or 142/142/142/142 mmHg (closed circle, control condition). Asterisk (*) represents statistical significance when compared to all conditions at the given time point (ttest, p<0.05). Data are presented as mean±standard deviation of six independent samples.
Figure 18:
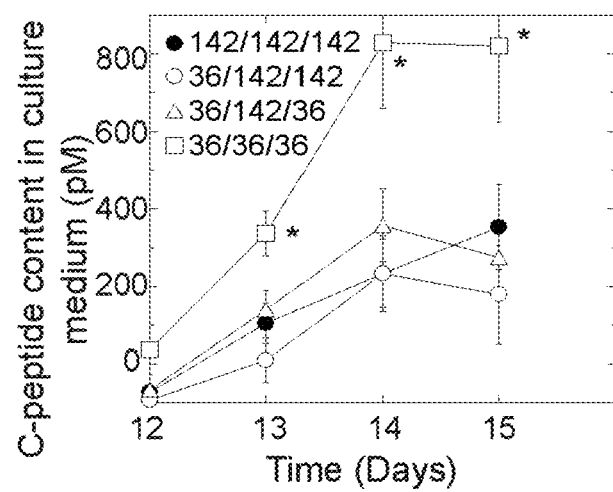
FIG. 18. Measurements of C-peptide content in culture media for CyT49 hESC. CyT49 hESC were differentiated during stage 1/2/3/4 at 36/142/142/142 mmHg (open circle), 36/142/36/142 mmHg (open triangle), 36/36/36/142 mmHg (open triangle) or 142/142/142/142 mmHg (closed circle, control condition). Asterisk (*) represents statistical significance when compared to all conditions at the given time point (ttest, p<0.05). Data are presented as mean±standard deviation of six independent samples.
Figure 19:
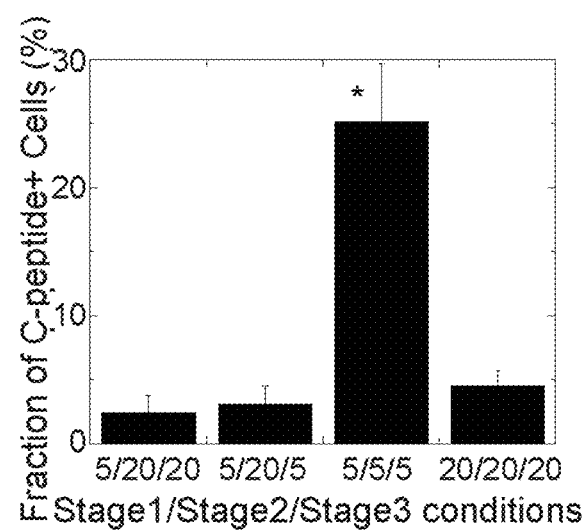
FIG. 19. Measurements of Insulin+ cells at day 15 (stage 5). CyT49 hESC were differentiated during stage 1/2/3 at the oxygen conditions shown and then stage 4 and 5 were performed at 20% oxygen. Asterisk (*) represents statistical significance when compared to all conditions at the given time point (ttest, $p<10^{-5}$). Data are presented as mean±standard deviation of six independent samples.

After 8 days of differentiation to PF, we saw that case 3 produced the largest percentage of PDX1+ cells, as measured by flow cytometry. (FIG. 15) However, there was no statistical difference between the four cases due to a large standard deviation in case 4. There is no statistical difference between cases 1-3 until day 15 for all PF and PE markers (FIG. 16). On day 15, Case 3 results in a factor of at least 1.3, 2.5, and 2.5 higher expression of PDX1, NKX6.1, and NKX2.2, respectively, when compared to either case 1 or case 2. Case 3 differentiation also resulted in a factor of 2 increase of Insulin and Glucagon gene expression when compared to case 1 and 2 differentiation conditions (FIG. 17). C-peptide in the culture medium, measured with ELISA, was first detected on day 12 for all but the control condition. Case 3-derived PF resulted in a factor of 2.3 more C-peptide released when compared to the next closest case, measured by Elisa (FIG. 18). Case 3 resulted in the most C-peptide+ cells seen to date with 25% of the cell being C-peptide+, a factor of 5 times larger than the other conditions, measured with flow cytometry (FIG. 19). With immunocytochemistry, we observed that many cells that were Insulin+ were also Glucagon+ and all Insulin+ cells were C-peptide positive (data not shown). The data indicate that culture at 36 mmHg $pO_{2gas}$ during the first three stages of differentiation followed by differentiation at 142 mmHg during stage 4 and 5 produces more C-peptide+ cells, and the largest gene expression of PE markers and Insulin.

We further investigated the effects of $pO_{2gas}$ during differentiation from PF to PE. The cells were differentiated at 36 mmHg through the first three stages, then at 285, 142, 71, 36, 21, and 7 mmHg $pO_{2,gas}$ for stage 4, and finally at 142 mmHg $pO_{2,gas}$ for stage 5 in order to examine c-peptide/insulin expression. Another set of cells were differentiated at 142 mmHg $pO_{2,gas}$ for all stages to act as a control. Using flow cytometry to examine the amount of c-peptide positive cells we discovered that if $pO_{2,gas}$ was reduced below 36 mmHg in stage 4, there was no increase in c-peptide+ cells compared to earlier results. However, in the range of 36 to 285 mmHg $pO_{2,gas}$ for stage 4, the fraction of c-peptide+/ insulin+ cells jumped by a factor of four to a mean of 34% (Table 1).

TABLE 1

Fraction of cells that were c-peptide+ and/or insulin+ (Mean ± SD)

| Conditions* | C-peptide+/ Insulin+ (%) |
|---|---|
| 20-20-20-20 | 4 ± 1 |
| 5-20-20-20 | 9 ± 4 |
| 5-5-20-20 | 8 ± 2 |
| 5-5-5-(1 to 3) | 8 ± 7 |
| 5-5-5-(5 to 40) | 34 ± 13 |

*percent $O_2$ in sequential stages

Table 1 summarizes the results for 9 of the 12 sequences in terms of the pooled mean of the fractions of cells that are c-peptide+ and insulin+ cells. Data are presented as the mean+/− standard deviation of multiple runs of a given set of conditions, where n>2.

With normoxic conditions in all of the stages (designated 20-20-20-20), the fraction was about 4%. Reduction of $O_2$ to 5% in stage 1 caused the fraction to double. A similar additional reduction of $O_2$ in stage 2 had no further effect. The effect of another sequential reduction to 5% in stage 3 depended on the oxygen level in stage 4. If $O_2$ was further reduced below 5% in stage 4, there was no change. However, in the range of 5 to 40% $O_2$ for stage 4, the fraction of c-peptide+/insulin+ cells jumped by a factor of four to a mean of 34%. At two conditions, the fraction was about 50%, but there was not a monotonic trend with $O_2$ level.

Figure 20:
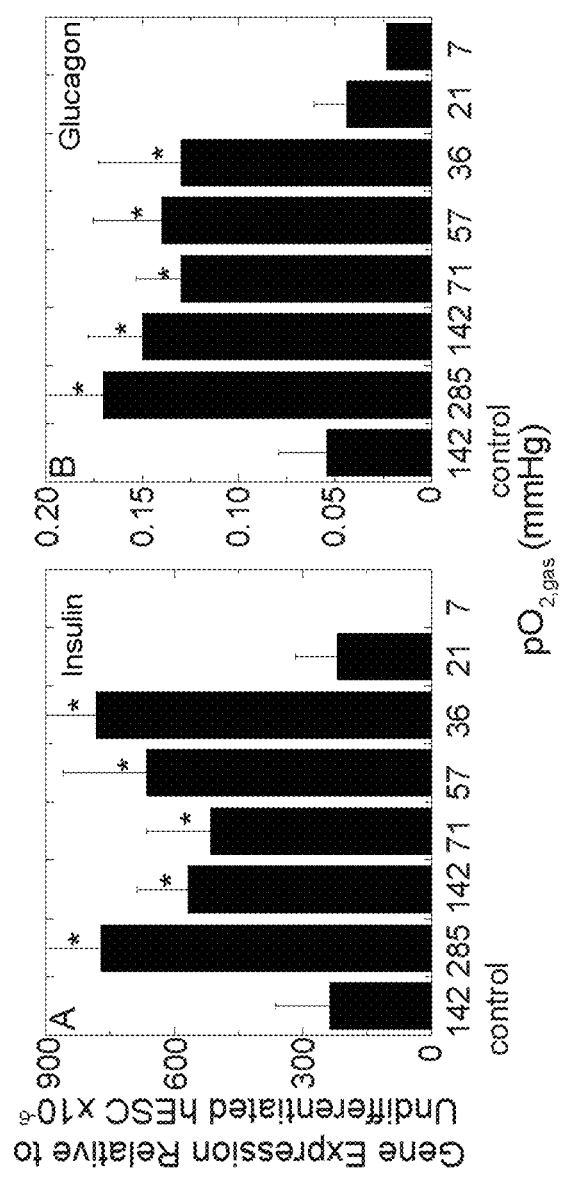
FIG. 20. Gene expression of the Insulin (A) and Glucagon (B) on day 15. CyT49 hESC were differentiated during stage 1-3/4 at 36 or 142 mmHg followed by either 7, 21, 36, 57, 71, 142, 285 mmHg. Asterisk (*) represents statistical significance when compared the control condition of 142/142 (ttest, p<0.05). Data are presented as mean±standard deviation of six independent samples, except for day 15 7 mmHg n=1.
Figure 21:
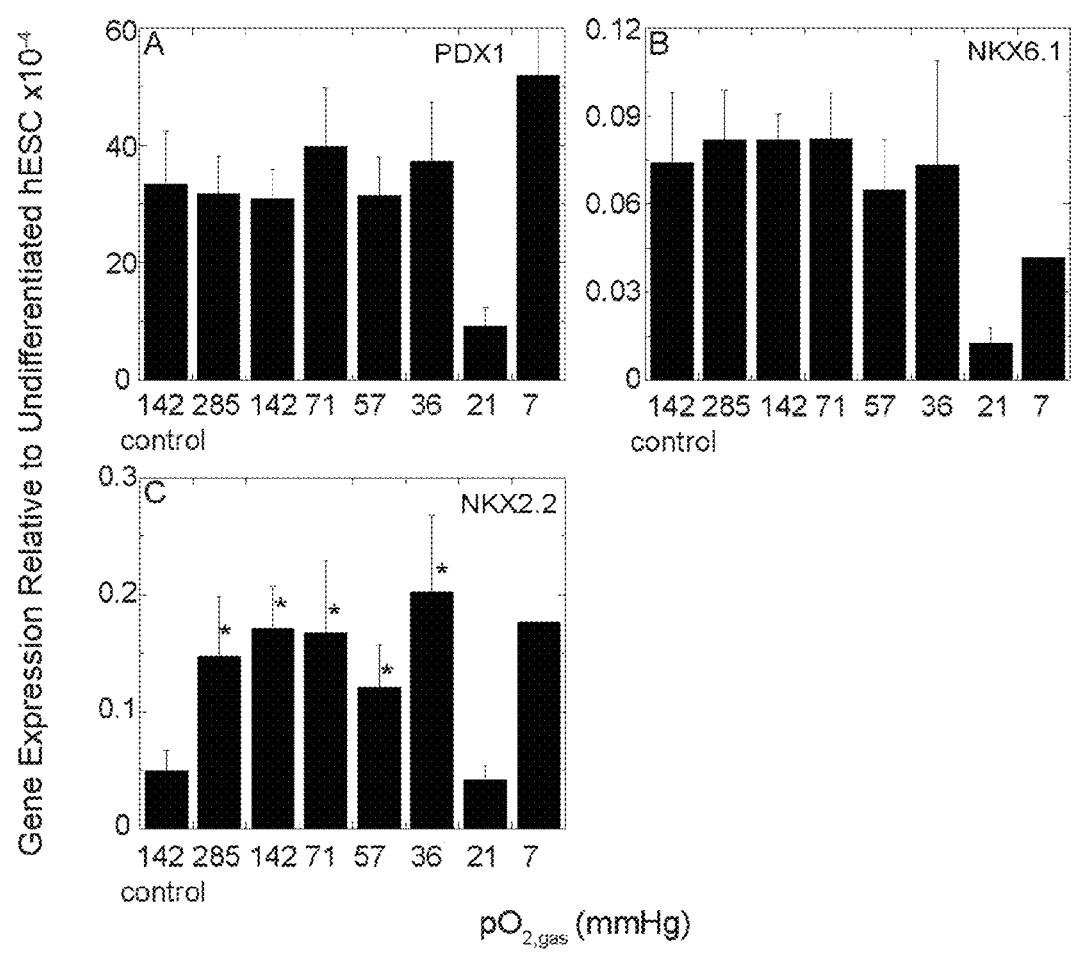
FIG. 21. Gene expression of the PDX1 (A), NKX6.1 (B) and NKX2.2 (C) on day 15. CyT49 hESC were differentiated during stage 1-3/4 at 36 followed by either 7, 21, 36, 57, 71, 142, 285 mmHg. Asterisk (*) represents statistical significance when compared the control condition of 142/142 (ttest, p<0.05). Data are presented as mean±standard deviation of six independent samples, except for day 15 7 mmHg n=1.

Examining gene expression of insulin and glucagon at day 15, there is at least a 2 fold increase for all oxygen conditions above 36 mmHg, when compared to a 142 mmHg differentiation control. (FIG. 20) The condition of 7 mmHg $pO_{2,gas}$ does have high gene expression but this is only for one sample due to spontaneous cell death resulting in the loss of samples. Examining markers for both PF and PE at day 15, we see that there is a slight increase in gene expression compared to 142 mmHg control; however, only the trend in NKX2.2 was statistically significant (FIG. 21). The data indicate that low oxygen during differentiation to PF followed by oxygen higher than 36 mmHg during differentiation to PE results in an increase of insulin expression.

These results demonstrated that modulation of the $O_2$ level to which cells are exposed can have a pronounced effect on the outcome of directed differentiation protocols. Culture at reduced oxygen for the first three stages, followed by an increase in $pO_{2,gas}$ levels for the last two stages, produced an eight-fold increase in the fraction of c-peptide+/ insulin+ cells.

The methods require exposure of ES cells to low oxygen partial pressure ($pO_2$). The invention relates to the use of low $pO_2$ during culture, and more particularly differentiation, of ES cells. Some embodiments of the invention relate to the use of gas phase $pO_2$ (i.e., $pO_{2gas}$) that is less than atmospheric partial pressure. $pO_{2gas}$ is DO is the partial pressure of oxygen in the gas phase, for example, in a culture incubator. Thus, this pressure is the pressure that cells in contact with the gas phase are exposed to. If the cells grow in a non-monolayer manner (e.g., in layers, spheres, or aggregates), then they will not be evenly exposed to the gas phase. As a result, some cells may be exposed to $pO_{2gas}$ while others (e.g., those situated within a sphere or aggregate) may be exposed to a $pO_2$ that is less than $pO_{2gas}$.

$pO_2$ can be measured in mmHg. Oxygen control devices may express oxygen levels as a percentage. $pO_{2gas}$ can be determined based on knowledge of a percent oxygen measurement using the following formula:

$$pO_2 = (\% \text{ oxygen}) \times (760-47)$$

In this equation, 760 is the atmospheric pressure and 47 is the vapor pressure of water at 37° C.). The equation assumes absolute % oxygen (e.g., air is 20% oxygen). Gas phase oxygen concentrations of 1%, 5%, 20%, and 40% correspond to $pO_{2gas}$ of 7 mmHg, 36 mmHg, 142 mmHg, and 285 mmHg. Atmospheric $pO_2$ is therefore about 142 mmHg.

In many cases, during cell culture in bioreactors, the % oxygen is actually given as % of air saturation. The equation to convert between the two is $$\% \text{ absolute} = \% \text{ air saturation} \times 0.2$$

The oxygen partial pressure within a cell is referred to herein as $pO_{2cell}$. $pO_{2cell}$ depends on several factors including medium depth, cell density, cellular oxygen consumption rate, and $pO_{2gas}$.

Cell culture is typically performed in a humidified environment consisting of 95% air and 5% $CO_2$ and this results in a $pO_{2gas}$ of about 142 mmHg. In the context of the invention, low $pO_2$ refers to $pO_2$ that is less than atmospheric partial pressure. In some embodiments, low $pO_2$ refers to a $pO_2$ that is less than 50 mmHg. Low $pO_2$ therefore may be a $pO_2$ that is less than 40 mmHg, or less than 30 mmHg. Low $pO_2$ may be a $pO_2$ in the range of 30-50 mmHg, 30-40 mmHg, 35-50 mmHg, and 35-40 mmHg, including every integer therebetween. In some embodiments, the $pO_2$ (whether gas or cell) is about 36 mmHg.

The invention contemplates in some aspects the use of a multi-step culture method for generation of C-peptide+ and/or insulin+ cells from ES cells. A five stage method is known in the art and provided by D'Amour et al. (*Nat. Biotechnol.* 24, 1393-1401 (2006)), the entire contents of which are incorporated by reference herein. A similar method is provided in U.S. published patent application US 20070259421, the entire contents of which are incorporated by reference herein. FIG. 1 illustrates this culture method. Briefly, this method involves 5 stages. Stage 1 involves culturing embryonic stem cells for two days during which time the cells differentiate into definitive endoderm (DE). Stage 2 involves further culture for another 3 days to generate primitive gut tube (PFT). Stage 3 involves further culture for another 3 days to generate posterior foregut (PF). Stage 4 involves further culture for another 4 days to generate pancreatic endoderm (PE). Stage 5 involves still further culture for another 4 days to generate insulin+ and/or C-peptide+ cells. In total, the cells are cultured for about 16 days, although they may be cultured for longer periods in some instances. FIG. 1 also shows the markers that can be detected at each stage. Markers of each of the stages of development are also described by D'Amour et al. (*Nat. Biotechnol.* 24, 1393-1401 (2006)) and U.S. published application US 20070259421. These are discussed in greater detail herein. As used herein, the terms "producing" and "generating" are used interchangeably.

In accordance with the invention, Stages 1-3 are preferably carried out low $O_2$, and Stages 4 and 5 are carried out at a higher $O_2$. The low $O_2$ is about 5% $O_2$ in some embodiments. The higher O₂ is more than 5%, and may range from 5% to 40%. In some embodiments, the higher O₂ is about 20% O₂. Thus, in some embodiments, Stages 1-5 of culture are carried out at 5%, 5%, 5%, 20%, and 20% O₂ respectively.

Cells may be kept in a single culture vessel during the stages of differentiation or they may be transferred to one or more successive culture vessels during the culture method. If kept within a single vessel, they may be washed between stages in order to remove culture ingredients such as those shown in FIG. 1.

$pO_{2gas}$ can be regulated during culture using manual and automated devices. Examples of commercially available automated devices include but are not limited to Oxycycler C42 from BioSpherix (Redfield, N.Y.) and MCO-5M from Sanyo (Bensenville, Ill.).

Various modifications to the culture system may be performed in order to reduce the disparity between $pO_{2gas}$ and $pO_{2cell}$. For example, convective oxygen transport in mechanically mixed or perfused vessels may be used. Alternatively or additionally, oxygen-permeable culture vessels such as oxygen-permeable dishes (e.g., F-dishes) may be used. Still another way of equilibrating $pO_{2gas}$ and $pO_{2cell}$ is through the use of oxygen-permeable membranes. As used herein, an oxygen-permeable membrane is a membrane that has an oxygen permeability greater than that of a standard (e.g., polystyrene) culture dish. One example of an oxygen-permeable membrane is a fluoroethylene-propylene copolymer (FEP-Teflon) membrane. Culture vessels comprising this membrane are commercially available as Lumox dishes (Greiner Bio-One, Munich). Another example is a silicone rubber membrane, which is used in the Examples. The oxygen permeabilities of FEP Teflon and silicone rubber are $0.2$-$0.4 \times 10^{-14}$ and $26 \times 10^{-14}$ mol cm$^{-1}$ mmHg$^{-1}$ sec$^{-1}$, respectively.

The oxygen-permeable membrane may be coated with an agent that promotes cell adhesion. The agent may be fibronectin, gelatin or laminin, or combinations thereof, although it is not so limited.

Silicone rubber membrane-based dishes may be prepared using the following exemplary protocol. Most of the bottom surface of the 8 central wells of 24-well tissue culture plates (353047, Becton Dickinson) is removed using a ⅜×3 inch fixed handle nutdriver (12, Cooper Hand Tools, Apex, N.C.) heated in a Bunsen burner to melt a hole in the plastic. A sterile scalpel is used to trim the edges of the holes. A very thin layer of silicone adhesive (59530, Henkel Loctite Corp., Rocky Hill, Conn.) is spread around each of the holes. A rectangular 8.5×4.5 cm piece of silicone rubber membrane (non-reinforced vulcanized gloss/gloss 0.005 inch, Specialty Manufacturing, Saginaw, Mich.), previously sterilized by autoclaving, is placed over the holes and manually pressed and stretched so that the silicone sheet is flat (no wrinkles) and sealed onto the plate bottom. After allowing the adhesive to cure for 24 hours, the plates are completely filled with a 70% ethanol solution for 1 hour and dried overnight under a germicidal UV lamp in a biological safety cabinet.

Gas phase pO₂ control may be achieved using the following exemplary method. Cell culture vessels are placed inside sealed polystyrene chambers (MIC-101, Billups-Rothenburg, Del. Mar, Calif.) that are housed inside a standard incubator (OWJ2720A, Queue Systems, Parkersburg, W. Va.) maintained at 37° C. The desired $pO_{2gas}$ is established and maintained using premixed gas containing 5% CO₂ and the desired oxygen level (e.g., 20%, 5% oxygen) (certified medical gas from Airgas, Hingham, Mass.). The flow rate of gas to the chambers is 2 l/min for 15 min for an initial purge following closure of the chamber (after cell medium exchange) and 30 ml/min at all other times. Gas is bubbled through a sealed bottle of water (in the incubator), and an open dish of deionized water in each chamber is provided for additional humidification.

As used herein, ES cells are pluripotent cells isolated from the inner cell mass of blastocysts and propagated in vitro. These cells have the capacity to differentiate into any cell type in the body. ES cells of the invention therefore have been isolated from their natural environment (i.e., the blastocyst). That is, they have been physically separated from the blastocyst.

In some embodiments, the ES cells are untransfected (i.e., they have not been genetically manipulated after their establishment to comprise or express an exogenous nucleic acid). The ES cells may be murine or human ES cells.

A number of ES cell lines currently exist. These include murine ES cell lines such as J1, R1, D3, CCE, SCC10, B6/Blu, EDJ22, and B6/GFP, and human ES cell lines such as BG01, BG02, BG03, SA01, SA02, ES01, ES02, ES03, ES04, ES05, ES06, H1, TE03, TE04, TE06, UC01, UC06, WA01, WA07, WA09, WA13 and WA14, all of which are available from public sources such as the NIH Human ES Cell Registry.

In addition, protocols for generating ES cells and lines are known in the art. The generation of murine ES cells and lines has been described. See for example Teratocarcinomas and ES cells: a practical approach (1987). E. J. Robertson, editor. IRL Press. and Wernig et al. Nature. 2007 Jun. 6 (online publication). U.S. Pat. Nos. 5,843,780 and 6,200,806 assigned to WARF describe the generation of human ES cells.

ES cell culture conditions are also known in the art. See for example Keller, ES Cell Differentiation: Emergence of a New Era in Biology and Medicine, Gene Dev., 19:1129-1155, 2005. These culture conditions either maintain ES cells in an undifferentiated state or cause differentiation of ES cells into one or more lineages. Culture of ES cells in an undifferentiated state usually requires the presence of feeder cells, although it can also be performed on gelatin-coated tissue culture plates. (Zandstra et al., Tissue Eng., 9(4):767-778, 2003). Such feeder cells are typically mitotically inactivated for example via irradiation or treatment with mitomycin C. Suitable feeder cells for murine ES cells include embryonic fibroblasts. In certain culture conditions, leukemia inhibitory factor (LIF) can replace the requirement for feeder cells. A suitable medium for these cultures is high glucose DMEM supplemented with 10% ES cell qualified FBS.

Human ES cells can be grown and maintained in an undifferentiated state in serum-free media (e.g., DMEM/F12 medium containing 20% KnockOut serum replacement (Invitrogen), 1 mM L-glutamine (Sigma), 2-mercaptoethanol, and 1× non-essential amino acids (Sigma)) in the presence of feeder cells and bFGF (4 ng/ml, Invitrogen). Feeder cells in these cultures may be substituted with matrigel- or laminin-coated plates using conditioned medium from mouse embryonic fibroblasts.

Such culture methods yielded a population of cells that was more than 30% insulin+ and/or C-peptide+. In some embodiments, the population was more than 40% insulin+ and/or C-peptide+. In some embodiments, the population was about 50% insulin+ and/or C-peptide+. The invention embraces the cells generated (or produced) using the differentiative methods provided herein.

Thus, in another aspect, the invention provides an in vitro cell culture comprising human cells wherein at least 30% of the cells are pancreatic islet hormone-expressing cells (e.g., insulin+ cells and/or C-peptide+ cells), and the cells are derived in vitro from human pluripotent cells such as human embryonic stem cells. In some embodiments, at least or about 34% of the cells are insulin+ and/or C-peptide+. In some embodiments, at least or about 50% of the cells are insulin+ and/or C-peptide+.

Thus, in still a further aspect of the invention, the differentiated cells can be administered to subjects alone or in combination with another active agent or in some embodiments an inactive agent. Examples include scaffolds that may function simply as a structural support for the cells to be administered. The cells may be administered to subjects in need thereof, including for example subjects having type I diabetes.

The differentiated cells may be formulated as pharmaceutical compositions that are sterile and appropriate for in vivo use. They may therefore be formulated in pharmaceutically acceptable carriers, with which the art is familiar. They may further be included in a kit that additionally comprises at a minimum instructions for use of the cells, and optionally comprises one or more other agents whether active or inactive.

Other Embodiments

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Each reference referred to herein is incorporated by reference herein in its entirety.

What is claimed is:

1. A method for producing insulin+ and/or C-peptide+ cells, comprising
   (1) differentiating human pluripotent stem cells to posterior foregut endoderm in vitro, at an oxygen partial pressure to which cells are exposed ($pO_{2\,cell}$) that is greater than 7 mmHg and less than 142 mmHg, in the presence of a TGF-β superfamily member and a retinoic acid receptor agonist, and
   (2) differentiating posterior foregut endoderm to insulin+ and/or C-peptide+ cells at a $pO_{2\,cell}$ that is 142 mmHg or higher.

2. The method of claim 1, wherein the human pluripotent stem cells are differentiated on an oxygen permeable membrane.

3. The method of claim 2, wherein the oxygen permeable membrane is an oxygen permeable silicone rubber membrane.

4. The method of claim 2, wherein the oxygen permeable silicone rubber membrane is coated with extracellular matrix (ECM).

5. The method of claim 1, wherein the iman pluripotent stem cells are human embryonic stem cells.

6. A method for producing insulin+ and/or C-peptide+ cells comprising
   (1) differentiating human pluripotent stem cells to definitive endoderm in the presence of a TGF-β superfamily member at a $pO_{2cell}$ that is in a range of 7 mmHg to 57 mmHg,
   (2) differentiating definitive endoderm to posterior foregut endoderm in the presence of a retinoic acid receptor antagonist at a $pO_{2cell}$ that is in a range of 21 mmHg to 71 mmHg, and
   (3) differentiating posterior foregut endoderm to insulin+ and/or C-peptide+ cells at a $pO_{2cell}$ that is 142 mmHg or higher.

7. The method of claim 6, wherein the the $pO_{2cell}$ of step (1) is 36 mmHg.

8. The method of claim 6, wherein the $pO_{2cell}$ of step (2) is 36 mmHg.

9. The method of claim 6, wherein the the $pO_{2cell}$ of step (3) is 142 mmHg.

10. The method of claim 6, wherein the the $pO_{2cell}$ of step (3) is higher than 142 mmHg.

11. The method of claim 1, wherein the $pO_{2cell}$ of step (1) 36 mmHg.

12. The method of claim 6, wherein the human pluripotent stem cells are human embryonic stem cells.

13. The method of claim 1, wherein the $pO_{2cell}$ of step (1) is 7 mmHg to 57 mmHg.

14. The method of claim 1, wherein the $pO_{2cell}$ of step (1) is 21 mmHg to 57 mmHg.

15. The method of claim 1, wherein the $pO_{2cell}$ of step (2) is 142 mmHg.

16. The method of claim 1, wherein the $pO_{2cell}$ of step (2) is higher than 142 mmHg.

* * * * *

UNITED STATES PATENT AND TRADEMARK OFFICE
CERTIFICATE OF CORRECTION

PATENT NO. : 9,447,378 B2
APPLICATION NO. : 13/873020
DATED : September 20, 2016
INVENTOR(S) : Clark K. Colton et al.

Page 1 of 1

It is certified that error appears in the above-identified patent and that said Letters Patent is hereby corrected as shown below:

On the Title Page

The Inventor Section should be corrected to read as follows:
(72) Inventors: Clark K. Colton, Newton, MA (US)
Amanda DiIenno, Boston, MA (US)
Jeffrey R. Millman, St. Louis, MO (US)

In the Claims

Column 15, Line 4, please delete "stern cells" and replace with "stem cells"

Column 15, Line 22, please delete "iman" and replace with "human"

Column 16, Line 8, please delete "the the" and replace with "the"

Column 16, Line 12, please delete "the the" and replace with "the"

Column 16, Line 14, please delete "the the" and replace with "the"

Signed and Sealed this
Thirty-first Day of December, 2019

Andrei Iancu
*Director of the United States Patent and Trademark Office*